United States Patent
Call et al.

(10) Patent No.: US 7,265,669 B2
(45) Date of Patent: Sep. 4, 2007

(54) NETWORKS WITH SENSORS FOR AIR SAFETY AND SECURITY

(75) Inventors: Charles John Call, Albuquerque, NM (US); Robert Beckius, Grants Pass, OR (US); Ezra Merrill, Albuquerque, NM (US)

(73) Assignee: MesoSystems Technology, Inc., Albuquerque, NM (US)

( * ) Notice: Subject to any disclaimer, the term of this patent is extended or adjusted under 35 U.S.C. 154(b) by 500 days.

(21) Appl. No.: 10/791,057

(22) Filed: Mar. 1, 2004

(65) Prior Publication Data

US 2005/0190058 A1    Sep. 1, 2005

(51) Int. Cl.
  *G08B 1/08* (2006.01)
(52) U.S. Cl. ............. 340/539.26; 340/506; 340/517; 340/521; 340/522; 340/533
(58) Field of Classification Search ........... 340/539.26, 340/506, 517, 521, 522, 531, 532, 533; 702/19, 702/22
See application file for complete search history.

(56) References Cited

U.S. PATENT DOCUMENTS

| | | | |
|---|---|---|---|
| 3,001,914 A | 9/1961 | Andersen | 435/30 |
| 3,518,815 A | 7/1970 | McFarland et al. | 73/863.22 |
| 3,633,405 A | 1/1972 | Noll | |
| 3,760,630 A | 9/1973 | Brumbaugh | 73/28.05 |
| 3,901,798 A | 8/1975 | Peterson | 209/143 |
| 3,922,905 A | 12/1975 | Roth | 73/28.04 |
| 3,972,226 A | 8/1976 | Rountree et al. | |
| 3,997,297 A | 12/1976 | Jenkins et al. | 23/232 E |
| 4,111,049 A | 9/1978 | Lerner et al. | 73/421.5 R |
| 4,301,002 A | 11/1981 | Loo | 209/143 |
| 4,473,384 A | 9/1984 | Lefkowitz | 55/290 |
| 4,580,440 A | 4/1986 | Reid et al. | 73/23 |
| 4,670,135 A | 6/1987 | Marple et al. | 209/143 |
| 4,697,462 A | 10/1987 | Daube, Jr. et al. | |
| 4,764,186 A | 8/1988 | Langer | |
| 4,767,524 A | 8/1988 | Yeh et al. | 209/143 |
| 4,820,920 A | 4/1989 | Bather | 250/282 |
| 4,941,899 A | 7/1990 | Liu | |
| 4,942,297 A | 7/1990 | Johnson et al. | |
| 4,961,966 A | 10/1990 | Stevens et al. | 427/299 |
| 4,987,286 A | 1/1991 | Allen | 219/121.68 |
| 4,990,740 A | 2/1991 | Meyer | |
| 5,039,490 A | 8/1991 | Marsoner et al. | |

(Continued)

FOREIGN PATENT DOCUMENTS

JP      59196713      11/1984

OTHER PUBLICATIONS

Carrano, John. "*Ultraviolet Light.*" Spie's Oe magazine, Jun. 2003, pp. 20-23.

(Continued)

*Primary Examiner*—Daryl C Pope
(74) *Attorney, Agent, or Firm*—Ronald M. Anderson

(57) ABSTRACT

Airborne particles are impacted on a collection surface, analyzed, and then the collection surface is regenerated. Thus, the same collection surface can be used in numerous cycles. The analysis can be focused on one or more properties of interest, such as the concentration of airborne biologicals. Sensors based on regenerative collection surfaces may be incorporated in many networks for applications such as building automation.

43 Claims, 9 Drawing Sheets

U.S. PATENT DOCUMENTS

| | | |
|---|---|---|
| 5,040,424 A | 8/1991 | Marple et al. |
| 5,063,164 A | 11/1991 | Goldstein |
| 5,128,539 A | 7/1992 | Rodgers et al. |
| 5,254,861 A | 10/1993 | Carpenter et al. |
| 5,299,141 A | 3/1994 | Hungerford et al. ......... 364/510 |
| 5,304,125 A | 4/1994 | Leith ........................... 604/57 |
| 5,412,975 A | 5/1995 | Raabe et al. |
| 5,425,802 A | 6/1995 | Burton et al. |
| 5,472,645 A | 12/1995 | Rock et al. |
| 5,498,271 A | 3/1996 | Marple et al. |
| 5,512,216 A | 4/1996 | Rock et al. |
| 5,533,406 A | 7/1996 | Geise ...................... 73/863.22 |
| 5,553,795 A | 9/1996 | Tsai et al. |
| 5,585,575 A | 12/1996 | Corrigan et al. ......... 73/863.71 |
| 5,760,314 A | 6/1998 | Bromberg et al. ....... 73/863.21 |
| 5,776,754 A | 7/1998 | Caldwell ................. 435/240.2 |
| 5,786,894 A | 7/1998 | Shields et al. .............. 356/338 |
| 5,932,795 A | 8/1999 | Koutrakis et al. ......... 73/28.01 |
| 5,949,001 A | 9/1999 | Willeke ..................... 73/865.5 |
| 6,024,923 A | 2/2000 | Melendez et al. |
| 6,062,392 A | 5/2000 | Birmingham et al. ....... 209/143 |
| 6,101,886 A | 8/2000 | Brenizer et al. ......... 73/863.23 |
| 6,110,247 A | 8/2000 | Birmingham et al. ......... 55/442 |
| 6,125,845 A | 10/2000 | Halvorsen et al. ..... 128/200.24 |
| 6,194,731 B1 | 2/2001 | Jeys et al. ................ 250/461.2 |
| 6,217,636 B1 | 4/2001 | McFarland ................... 95/216 |
| 6,235,002 B1 | 5/2001 | Carver et al. ............... 604/183 |
| 6,240,768 B1 | 6/2001 | Lemmonnier .............. 73/28.05 |
| 6,267,016 B1 | 7/2001 | Call et al. |
| 6,276,016 B1 | 8/2001 | Springer ..................... 14/71.1 |
| 6,284,025 B1 | 9/2001 | Kreisberg et al. ............. 95/267 |
| 6,324,927 B1 | 12/2001 | Ornath et al. ............ 73/863.11 |
| 6,334,365 B1 | 1/2002 | Linker et al. ............ 73/864.81 |
| 6,363,800 B1 | 4/2002 | Call et al. |
| 6,435,043 B1 | 8/2002 | Ferguson et al. ........ 73/863.22 |
| 6,511,854 B1 | 1/2003 | Asanov et al. |
| 6,573,836 B1 | 6/2003 | Gitis et al. .................. 340/603 |
| 6,695,146 B2 | 2/2004 | Call et al. ................ 73/863.22 |
| 6,707,539 B2 | 3/2004 | Selinfreund et al. |
| 6,805,751 B2 | 10/2004 | Allen ............................. 134/1 |
| 6,908,567 B2 | 6/2005 | Uziel .......................... 216/66 |
| 6,949,147 B2 | 9/2005 | Uziel et al. ..................... 134/1 |
| 7,096,125 B2 * | 8/2006 | Padmanabhan et al. ....... 702/24 |
| 2004/0028561 A1 | 2/2004 | Daugherty et al. .......... 422/99 |

OTHER PUBLICATIONS

Cassarly, William. *"Taming Light." "Non-imaging optical systems focus on transferring light efficiently and controlling its distribution."* Oe magazine, 7pp. <http://www.oemagazine.com/fromTheMagazine/dec02/taminglight.html>.

Cousins, Daniel. *"Biodefense of Passenger Aircraft."* Biodefense Systems Group, MIT Lincoln Labroratory. Presented at FAA Center of Excellence. 23pp.

Foot, Virginia, E., et al. *"Characterising single airborne particles by fluorescence emission and spatial analysis of elastic scattered light."* Defence Science and Technology Lab. (United Kingdom) 2pp, 2005 Copyright SPIE-The international Society for Optical Engineering. <http://spiedl.aip.or/GetabsServlet?prog=normal&id=PSISDG00561700000 . . . >.

Frye-Mason, Greg et al. *"Novel fluorescence-based integrated sensor for chemical and biological agent detection."* Nomadics, Inc. (USA) 2pp, 2005 Copyright SPIE—The international Society for Optical Engineering. <http://spiedl.aip.or/GetabsServlet?prog=normal&id=PSISDG00561700000 . . . >.

Huston, Alan, L., et al. *"Optical classification of bioaerosols using UV fluorescence and IR absorption spectroscopy."* Naval Research Lab. (USA) 2pp, 2005 Copyright SPIE—The international Society for Optical Engineering. <http://spiedl.aip.or/GetabsServlet?prog=normal&id=PSISDG00561700000 . . . >.

Jeys, T.H., L., et al. *"Development of UV LED based biosensor."* SPIE vol. 5071, 2003 Copyright SPIE., pp. 234-240.

Kaye, Paul, H., et al. *"A low-cost multi-channel aerosol fluorescence sensor for networked deployment."* University of Hertfordshire (UK) and Defence Science Technology Lab (UK) 11pp, 2005 Copyright SPIE—The international Society for Optical Engineering. <http://spiedl.aip.or/GetabsServlet?prog=normal&id=PSISDG00561700000 . . . >.

* cited by examiner

```
410
preconditioning
air sample
    ↓
420
concentrating airborne particles of
desirable size range
    ↓
440                                    430
depositing airborne    ←    moistening
particles on a                collection surface
collection surface
    ↓
450
analyzing deposit on
collection surface
    ↓
470            460
verifying  ↔  regenerating the
regeneration   surface
```

FIG. 4

NETWORKS WITH SENSORS FOR AIR SAFETY AND SECURITY

FIELD OF INVENTION

The invention relates to methods and devices for continuous monitoring of airborne particles, airborne biological particles, and systems of monitoring air quality.

BACKGROUND OF INVENTION

Monitoring airborne particles is of concern in a number of civilian and military contexts. Airborne hazards can come in a variety of forms, for example, of biological, chemical, or radiological nature. Sometimes severe biological airborne perils may suddenly arise at unpredictable locations, such as in bio-terrorist attacks. The most efficient response to biohazards can be mounted based on their earliest practicable detection.

The typical problem facing the aerosol field is that of collecting and characterizing airborne particles. Characterization of these airborne particles can be performed in situ (i.e., while the particles remain suspended in a gas), or in extractive techniques where particles are collected and then deposited onto a solid substrate or into a liquid for the purpose of subsequent physical or chemical analysis.

Identifying biological materials in situ has been attempted by detection of autofluorescence of airborne bacteria. While autofluorescent properties may be useful in detecting biological particles, their in situ measurement is challenging for a number of reasons. It is particularly difficult to measure fluorescent characteristics of minuscule particles in an airborne state. The particles are available for analysis quite briefly, thus making it difficult to determine several informative characteristics. In addition, the equipment required comprises expensive powerful lasers and sensitive fluorescence photodetectors or photon counters. The resulting devices are large and expensive, making this technology unlikely to be adopted for some applications, such as routine monitoring of civilian buildings.

In alternative approaches, extractive instruments such as jet impingers, jet impactors, cyclones, and filters deposit particles onto substrates, which may be liquids, surfaces such as greased slides or agar-coated plates, or filters. The content of extracted particles can then be analyzed by any desirable technique. While analysis of airborne particles may be performed more thoroughly with extractive rather than in situ techniques, extractive techniques require consumables such as deposit substrates and/or analysis reagents and/or human involvement in the analysis. Continuous use of consumables and/or labor can become problematical and prohibitively expensive. Therefore, monitoring systems based on extractive techniques are also of questionable value for routine, continuous use.

There is a current need for devices and methods to continuously detect airborne particles. Continuous monitoring of the largest possible number of populated premises seems the most desirable option in dealing with the unpredictability of airborne biohazards emergence. Widespread adoption of such devices would allow protection of a large number of potentially endangered persons. For widespread adoption, however, such devices should be fairly inexpensive and reliable. Operation of the device should be automatic, i.e. not requiring any user input. In addition, to be used routinely in a large number of buildings airborne biohazard detection devices should ideally be maintenance free and use no consumables.

SUMMARY OF INVENTION

In one aspect the present invention relates to methods for continuously monitoring airborne particles. Continuous monitoring according to the invented methods is achieved through a plurality of cycles. The methods are suitable for monitoring a variety of airborne particles. In specific embodiments they are designed to monitor the presence or concentration of airborne hazards. Cycles according to the invented methods comprise a plurality of steps.

A step according to the present methods is depositing airborne particles on a collection surface. Accordingly, a spot is formed on the collection surface. Depositing airborne particles is preferably accomplished by impaction caused by directing an air stream at the collection surface. In a preferred embodiment, airborne particles in the 0.5-10 µm size range are retained in the spot, the airborne particles retained in the spot thus comprising biological particles. Some embodiments comprise the optional step of pre-concentrating airborne particles of a desirable size range, such as particles with sizes between about 0.5-10 µm, in the air stream prior to impaction on the collection surface. Some embodiments comprise the optional step of preconditioning the air stream by removing particles of an undesirably large size. For example, particles of sizes greater than 10 µm may be removed. In some embodiments, both preconditioning and pre-concentrating are performed, with the pre-conditioning preferably prior to the pre-concentrating step.

In some embodiments, a step prior to depositing airborne particles is moistening the collection surface. Many types of liquids may be used to moisten the collection surface including glycerol, alcohols, or medium weight hydrocarbons, such as octane. The precise volume of liquid used in each cycle depends on several different variables, but may be about 5 µl.

Another step of the invented methods comprises analyzing the spot. The type of analysis performed depends on the nature of the particles to be monitored. Preferably, analyzing is accomplished by measuring biological, chemical, and/or radiological properties of the spot. In some embodiments, a plurality of properties is measured for each collected spot. Appropriate measurements in various embodiments may be directed to fluorescence, infrared absorption, mass specter, Raman specter, gamma emission, alpha emission, or beta emission properties of the spot. In preferred embodiments, biological particles are monitored by measuring autofluorescence of the spot. In some embodiments, analyzing is preceded by an optional step of pre-treating the spot so as to enhance the measured signal. Thus, pre-treating may comprise adding to the spot a liquid comprising an analysis-enhancing compound, or plasma lysing. In some embodiments where analyzing is accomplished by Matrix Assisted Laser Desorption Ionization (MALDI) time-of-flight mass spectrometry, pre-treating may be performed by plasma lysing and adding matrix solution to the spot.

Another step of the invented methods comprises regenerating the collection surface. As a result of this step the spot is removed and the collection surface is made available for another cycle. Regeneration is achieved by any one or combination of steps. For example, in some embodiments, regeneration is accomplished by pressing a felt pad against the collection surface and moving the felt pad over the collection surface. In other embodiments a felt wheel is rotated while pressed against the collection surface. In other embodiments the collection surface is electrostatically charged as part of the regeneration step. In other embodiments regeneration is accomplished by brushing the collection surface with a brush. In other embodiments regeneration is accomplished by blowing an air jet at high velocity towards the collection surface. In other embodiments, regeneration is accomplished by scraping the collection surface with a blade. In other embodiments, regeneration is achieved with heat, electricity, lasers or other forms of energy directed at the regenerative surface.

In some embodiments all the cycles of the invented methods are identical, whereas in other embodiments cycles may comprise different steps. In some embodiments, the invented methods in at least a subset of cycles comprise verifying the regeneration of the surface. Accordingly, the collection surface is analyzed after regeneration (the regenerated collection surface) essentially by the same process of analyzing the spot. Thus a background signal level is obtained for the regenerated surface. For example, if analyzing the spot is by measuring its fluorescence properties, verifying may be by similarly measuring the fluorescence properties of the regenerated collection surface to obtain a background fluorescence level. The background signal level is then compared to predetermined criteria. If the background level is found to be higher than desirable, regeneration and verification is repeated until the background signal level meets predetermined criteria. Alternatively, verifying may employ a test different from that used in the analysis step.

In other aspects, the present invention relates to devices useful for continuously monitoring airborne particles. In different embodiments the devices serve to monitor of the presence and concentration of airborne hazards for example of a biological, chemical, or radiological nature. The devices comprise several components, which are present in different combinations in different embodiments.

One component of the invented devices is an impaction plate. One of its features is a collection surface, on which a spot of airborne particles gets collected when the devices are in operation. In some embodiments, the collection surface is smooth, and is therefore easily cleaned by a surface regenerator. In other embodiments, the collection surface comprises features that improve the collection efficiency of impacting airborne particles, such as pyramid-shaped structures of about 1-10 µm in height and width. In some embodiments, the impaction plate comprises more than one, i.e. a plurality of collection surfaces.

Another component of the invented devices is a spotting nozzle. The spotting nozzle directs an air stream towards the collection surface of the impaction plate. The resulting impact of the air stream produces a spot that contains airborne particles on the collection surface. In some embodiments a particle concentrator, such as a virtual impactor, is placed upstream of the spotting nozzle, which increases the concentration of airborne particles within a desirable size range. In some embodiments, a size selective inlet is placed upstream of the spotting nozzle, which eliminates airborne particles greater than a desirable size. In some embodiments, both a concentrator and a size selective inlet are present upstream of the spotting nozzle. In some embodiments the spotting nozzle is substantially vertical while the collection surface is substantially horizontal. In preferred embodiments the nozzle, impaction surface and air stream velocity are configured so that the spot is enriched in particles of about 0.5-10 μm sizes.

Another component of the invented devices is an analyzer, which can examine characteristics of the spot on the collection surface. In preferred embodiments the analyzer is a fluorescence detector that determines the intrinsic fluorescence characteristics of the spot. In other embodiments, the analyzer may be for example, an infrared absorbance detector, a mass spectrometer, a Raman spectrometer. Some embodiments comprise more than one analyzer. Thus, any means for analyzing the spot suitable for detecting a class of airborne particles may be employed.

In some embodiments, the invented devices comprise a pre-analysis spot preparation station. At this point the spot is prepared to enhance its characteristics measured by the analyzer. For example, the spot may be combined with compounds that affect measured properties of the airborne particles of interest by squirting a liquid containing the appropriate compound from an inkjet type of device. In one embodiment, the pre-analysis spot preparation station applies a plasma lysis pulse to the spot, which is then analyzed by MALDI mass spectrometry.

Another component of the present devices is a surface regenerator. This component removes the spot from the collection surface during operation of the devices, thus regenerating the surface. In some embodiments the regenerator is a felt pad that regenerates the collection surface by pressing against the collection surface while the pad and the collection surface move relative to each other. In some embodiments, the surface regenerator is a felt wheel that is pressed against the collection surface and simultaneously rotated by a coupled motor. In some embodiments the regenerator is a blade that regenerates the collection surface by scraping or wiping it. In some embodiments the surface regenerator is a brush that regenerates the surface by brushing or sweeping it. In some embodiments the surface regenerator is a regenerator nozzle that blows air at high velocity towards the collection surface, preferably at an angle. In some embodiments, the regenerator comprises means for electrostatically charging the collection surface, which loosens an attached spot. The regenerator may comprise any means for directing energy to the spot and/or collection surface. Useful energy forms include heat, electricity, or lasers. Some embodiments comprise more than one surface regenerator, which may be of similar or different types. Thus, any means for regenerating the collection surface may be employed.

Another component present in some embodiments is a liquid coating applicator. It moistens the collection surface prior to impaction of the airstream, and thus helps trapping airborne particles and enhances the collection efficiency. The liquid coating applicator may be, for example, a felt tip pen. It might alternatively be similar to inkjet printing devices. It comprises a reservoir of liquid to be applied to the collection surface. There are several types of liquids that may be used, including alcohol, glycerol, or a medium weight hydrocarbon such as octane.

Another component of the devices is a homing sensor. Its function is to operatively position the collection surface to the various device components present in different embodiments, including the liquid coating applicator if present, the spotting nozzle, the pre-analysis spot preparation station if present, the analyzer, and the surface regenerator. Thus, in operation the homing sensor can cyclically position the collection surface sequentially from the liquid coating applicator if present to the spotting nozzle to the analyzer, to the pre-analysis spot preparation station, and to the surface regenerator. In general, the invented devices may accomplish the function of positioning the collection surface to each present component by any means for translocating the collection surface relative to the other device components. For example, a prime mover may be coupled to a shaft to which the impaction plate is attached, and proper positioning of the collection surface is accomplished by rotation of the shaft at predefined angles.

The different components of the invented devices can take various shapes in specific embodiments. For example, the homing sensor may comprise a shaft attached to the impaction plate. A prime mover is coupled to the shaft, and the homing sensor functions by rotating the disk at predefined angles. Each rotation step operatively positions the collection surface to a component of the devices. In some embodiments, the impaction plate is a disk, and a shaft is positioned along the disk axis and bound to the disk. In another preferred embodiment, the impaction plate is a lobed cam, and the impaction surfaces on the side of the cam. The impaction surfaces are flat, and may be produced directly on the cam or created by flat inserts embedded in the cam. The preferred material for the insert is a material of high surface hardness, such as hard-anodized steel, quartz or sapphire.

In another aspect, the present invention relates to devices useful for detecting or measuring airborne biological particles. The devices may comprise a collection surface, typically a regenerative collection surface, which supports a spot of immobilized airborne particles. In many embodiments, the devices further comprise an inertial impactor that immobilizes the spot on the collection surface.

The invented devices comprise a detector that is capable of analyzing the content of the spot. Typically, the detector is capable of sensing a biological signature that is present in the spot. The biological signature is preferably autofluorescence of biomolecules, but any other known signature may be sensed, including various types of Raman, infrared absorption, or mass spectra. These biological signatures are detected with known devices such as fluorescence detectors, Raman spectrometers, Fourier transform infrared spectrometers, or MALDI mass spectrometers. In some embodiments, multiple detectors analyze the spot. As a result of analysis, the detector produces signals, typically electrical signals, which are indicative of the biological signature. Consequently, the detector may recognize the presence of specific biological materials or may measure the concentration of classes of biological materials.

Preferably, the detector is a fluorescence detector that measures the inherent fluorescence of biological particles. The fluorescence detector comprises an excitation light source, which emits an excitatory radiation towards the spot to be analyzed. Any available source of radiation may be used. In some embodiments, the excitation light source is a LED. The excitatory radiation is of wavelengths operative to excite biomolecules to produce fluorescence. In many embodiments, the excitatory radiation is substantially ultraviolet, and the fluorescence radiation may be substantially visible. For example, the excitatory wavelength may be within the 340-370 nm range, or it may be approximately 266 nm, or it may be approximately 400 nm.

Fluorescence detectors also comprise fluorescence photosensors, which measure the radiation emitted from the spot in response to excitation. Any available photosensor may be used. In some embodiments, the fluorescence photosensor is a photodiode. Fluorescence detectors may also comprise additional components, such as a dichroic mirror that substantially reflects excitatory radiation and is substantially transparent to fluorescence radiation. The dichroic mirror can be positioned to reflect the excitatory radiation towards the spot, and allow passage of the emission radiation to the photosensor. Other optical components may also be employed, such as an excitation filter positioned between the excitation light source and the dichroic mirror or spot, and an emission filter positioned between the dichroic mirror or spot and the fluorescence photosensor.

As mentioned above, the detector produces signals related to the biological signature detected. The signals are usually transmitted to a receiver, which may then relay the signals for further processing. The signals typically reach a processor, which may be a computer or a Neuron Chip®. The processor is capable to process or interpret the signals and thus establish or gauge the concentration of biological particles in the spot. Consequently, the processor is capable to establish when the concentration of biological particles in the spot exceeds a predetermined value. In such a case, the processor outputs an alarm signal that alerts users of the presence of potentially harmful levels of airborne biological particles.

In yet another aspect, the present invention is related to methods of detecting specific airborne particles or concentrations of airborne biologicals. The methods comprise a plurality of steps, which may be repeated cyclically to ensure continuous monitoring of environmental air. One step according to the invented methods is depositing airborne particles on a regenerative collection surface to form a spot, which may be accomplished by inertial impaction. Another step comprises measuring a biological signature present in the spot. Examples of biological signatures are provided above. Consequently the presence of concentration of airborne biological particles is determined from the measurement. Where the steps are preformed cyclically, each measurement generates a present value of the concentration of airborne biological particles. Values from preceding measurements may be at least temporarily stored and used in calculating the average value and the standard deviation from prior measurements. Thus, a defined number of prior values can be used calculating the average, for example eight, which are derived from measurements in the preceding cycles. The present value is then compared to the calculated average to determine if the present value exceeds the average to a significant extent. The standard deviation from the prior measurements can be used to establish if the present value is abnormally high. Thus, the present value may be compared to the average value plus a preset factor, for example between 3 and 8, multiplied by the standard deviation. If the present value does exceed the average value to a significant extent, then the processor outputs an alarm signal. Finally, another step is regenerating the collection surface.

In other aspects, the present invention comprises devices, systems such as for monitoring and controlling air quality, and networks such as control networks. Different facets of the invention relate to applications that improve, for example, buildings or public facilities, HVAC systems, airplanes, and generally result in overall safer premises. Sensors based on regenerative surface air samplers can be employed in monitoring airborne hazards. For example, biological, chemical, or radiological sensors can be set to continuously observe air quality. Sensors based on regenerative surface air samplers may be deployed as stand alone devices, but they may also be incorporated into smart or intelligent sensor networks.

The sensors communicate signals through a communication interface, which may be a transmitter in some embodiments. In other embodiments the communication interface is a transceiver. Signals are typically communicated over a control network such as a building automation system network. The communication interface or transceiver can communicate through a wired or wireless connection. In some embodiments, the transceiver communicates via an RF link to an RF link network.

In some embodiments, the sensor based on a regenerative sample may output a positive response that directly activates other devices, for example specific sensors capable of identification of specific chemical, biological, or radiological species or narrow classes of species, samplers capable of capturing and/or archiving samples of airborne particles, or other sensors that are not based on regenerative surfaces.

As mentioned above, the sensors preferably communicate to an automation system network, such as a LonWorks® automation system or a CEBus automation system. Preferably, a transceiver communicates through a standard protocol, such as the BACnet protocol or the LonTalk® protocol.

In many embodiments, a controller is communicatively coupled to the sensor. In some embodiments the controller is a Neuron® chip. Typically, the controller is also coupled to the transceiver. In some embodiments the controller is coupled to at least one actuator and capable of actuating at least one air management component in response to information received from the sensor. The controller may also be communicatively coupled to the air management component, and thus it may be able to receive and integrate information additional to that received from the sensor. Examples of air management components are air analysis devices such as sample capture devices, sample analysis devices, or particle counters, smoke or fire sensors, or air control devices such as air duct dampers.

In another aspect, the present invention relates to methods of constructing a sensors network. Accordingly, sensors based on a regenerative surface air sampler can be added into a network. The sensors may be of biological particles, or chemical or radiological sensors. The network may contain any number of additional components, such as smoke or fire sensors.

In yet another aspect the present invention relates to methods of controlling ambient air quality. According to the invented methods, ambient air is sampled with at least one sensor based on a regenerative surface air sampler. Sampling can take place continuously and automatically. If at one point sampling by the sensor indicates a probable threat, a responsive step is performed. The responsive step may comprise actuating at least one air management component, activating at least one specific sensor, issuing an alert signal. In case an alert signal is issued, it may be transmitted to one or several locations, such as facility management or a fire department or law enforcement agency creating a two-tier warning system.

BRIEF DESCRIPTION OF DRAWINGS

FIG. 4 is a diagram of a method for continuous monitoring of airborne biological particles.

DETAILED DESCRIPTION OF PREFERRED EMBODIMENTS

In one aspect, the invention relates to an apparatus or device for continuous monitoring of the concentration and content of airborne particles. One embodiment is diagramed in FIG. 2. Some components of the device are a spotting nozzle, an impaction plate, a detector, and a regenerator. Additional components are present in some embodiments, such as a virtual impactor and/or a liquid coating applicator.

The spotting nozzle accelerates air from an inlet onto the impaction plate where airborne particles are collected. By spotting nozzle is meant a jet through which a gas sample is passed and which increases the mean velocity of the gas sample to a value sufficient to impart enough momentum to particles above a specific size that the particles are able to impact on an impaction plate as described herein. For example, a gas sample may be sucked through a nozzle having a reduced cross-sectional area relative to a source of gas using a downstream vacuum pump. An acceleration nozzle may be of any shape, such as round or slit-shaped. A round acceleration nozzle or jet has a round opening through which gas exits. The nozzle body may be cylindrical. A slit-shaped acceleration nozzle or jet has a rectangular opening, including narrow and nearly square-shaped openings, through which gas exits.

Figure 1:
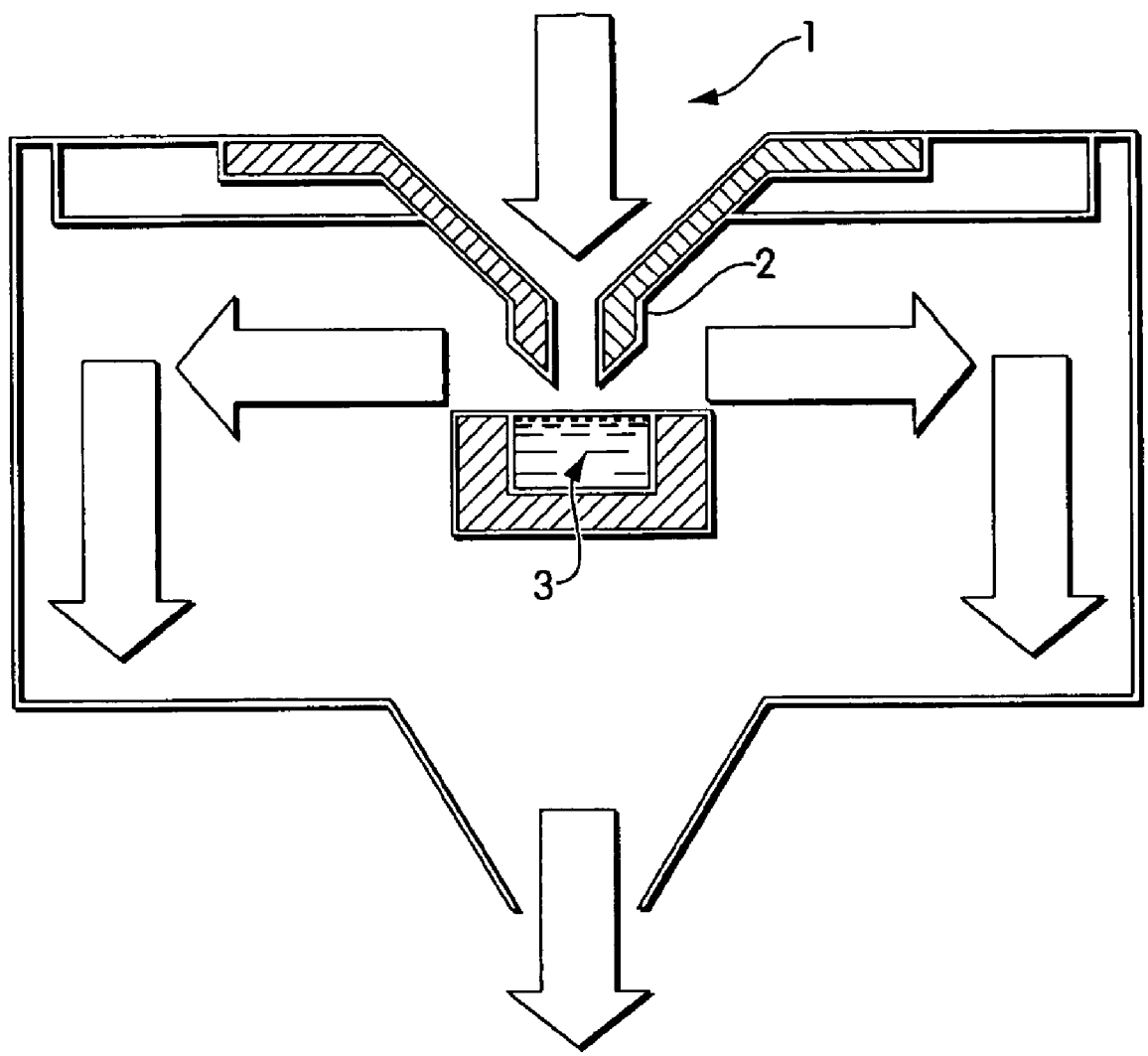
FIG. 1 is a diagram of a prior art inertial impactor.

Acceptable spotting nozzles have been used in inertial impactors. An exemplary inertial impactor is shown in FIG. 1. Accordingly, an air sample (1) is drawn through the inlet (2). The sample of air is drawn over the surface of the substrate (3), which collects particles having an inertia too great to follow the curved path of the air stream. The substrate, or impaction plate, according to the present invention is described below.

An inertial impactor typically refers to a single unit comprising of an air inlet, a spotting or acceleration nozzle, and an impaction plate. At the acceleration nozzle exit, the airstreams turns sharply and particles larger than a certain diameter (referred to as the impactor's cut-off size) impinge on the collection surface of the impaction plate due to inertial forces. Exemplary inertial impactors are discussed in U.S. Pat. Nos. 6,435,043, 5,553,795, 5,437,198, 4,926,679, 4,796,475, 4,321,822, and 4,133,202.

The physical principles of operation of an inertial impactor is similar to that of a virtual impactor referred to below. A jet of particle-laden air is deflected abruptly by an impaction plate, which causes an abrupt deflection of the air streamlines. Particles larger than a critical size (the so-called cutpoint of the impactor) cross the air streamlines and are collected on the impaction plate, while particles smaller than the critical size follow the deflected streamlines. The cutpoint of an impactor is determined by several parameters through the Stokes number.

$$St = \frac{\rho_p d_p^2 U C_c}{9 \eta D_j}$$

where $\rho_p$ is the particle density, $d_p$ is the particle diameter, U is the impactor jet velocity, $\eta$ is the gas viscosity, and $D_j$ is the diameter of the impactor jet (Hinds, "Aerosol Technology", 1982, John Wiley & Sons, Inc.). The slip correction factor, $C_c$, corrects for the reduced drag on small particles as they approach the mean free path of the gas. The collection efficiency for an impactor is often characterized by its D50, the diameter at which 50% of the input particles are collected.

The slip correction factor is given by the following equation:

$$C_c = 1 + \frac{2}{Pd_p}(6.32 + 2.01^{-0.1095 P d_p})$$

where P is the absolute pressure in Cm Hg and $d_p$ is the particle diameter in $\mu$m.

The preferred air velocity is greater than 10 m/s and less than 100 m/s, and more preferably greater than 20 m/s and less than 30 m/s. The nozzle diameter is preferably greater than 0.25 mm and less than 2.5 mm, and more preferably greater than 0.5 mm and less than 1 mm. The nozzle is preferably located a distance from the impaction surface greater than 0.1 mm and less than 2 mm, and more preferably, a distance greater than 0.25 mm and less than 0.5 mm.

Inertial impactors and impaction substrates used for collection of ambient particles are known to sometimes exhibit low particle collection efficiency. Low particle collection efficiency is a result of at least two factors: particles of high momentum impact the substrate and bounce off, and particles which have been previously collected are displaced from the substrate and re-entrained in the airstream (Sehmel, G. A., Environ. Intern., 4, 107-127 (1980); Wall, S., John, W., Wang, H. C. and Coren, S. L., Areosl. Sci. Technol., 12, 926-946 (1990); John, W., Fritter, D. N. and Winklmayr, W., J. Aerosol. Sci., 22, 723-736 (1991); John, W. and Sethi, V., Aerosol Sci. Technol., 19, 57-68 (1993)). In addition, because these two processes typically depend on particle size, the size distribution of the collected particles can be distorted.

Such problems, however, are not of significant concern for the invented devices. Precise knowledge of collection efficiency is not crucial for the present invention. The only requirement for the collection efficiency is that it does not vary widely or unpredictably with the concentration of airborne particles. Thus, under otherwise similar operating conditions, a larger number of particles should be collected into a spot from an air sample with a higher concentration of airborne particles. A spot is an aggregate of particulates deposited upon a surface in a relatively small area, so that the individually small particulates are aggregated together to form a larger spot. Moreover, as described below, the present invention provides for continuous monitoring of air samples. As a result, it is often detection of changes in the concentration and/or composition of airborne particles in air samples that is of interest. Detection of such changes is unaffected by a relatively low collection efficiency. Thus, the continuous monitoring feature of the present invention circumvents some of the shortcomings usually associated with inertial impactors.

For the same reason, variability of collection efficiency for particle of various sizes does not negatively impact the operation of the present invention. In a preferred embodiment, the inertial impactor is configured for optimum collection of particles in the 0.5-10 $\mu$m diameter, more preferably in the 1-5 $\mu$m range. Airborne particles in this range are the most likely to represent an inhalation hazards to humans. Within this range bacteria would be captured, as well as potentially noxious viruses or protein aggregates. However, the inertial impactor may be configured for optimal collection of particles of other size ranges in different applications.

In some embodiments, the intake of the spotting nozzle is downstream of a virtual impactor. By downstream it is mean that the second component (the spotting nozzle in this case) and the first component (the virtual impactor) are arranged so that the gas or air sample passes sequentially through the first and then the second component of the system. A virtual impactor is an apparatus that increases the concentration of airborne particles of a desirable size range. It separates an airflow into a minor and a major component, wherein the minor component carries a majority of airborne particles above a certain size. Examples of virtual impactors can be found in U.S. patent application Ser. No. 09/955,481, or in U.S. Pat. Nos. 3,901,798; 4,670,135; 4,767,524; 5,425,802; and 5,533,406. Thus, the spotting nozzle can be downstream of the minor flow of a virtual impactor. It is preferable that the virtual impactor increases the concentration of particles above 1 $\mu$m. In some embodiments, more than one virtual impactor is placed upstream of the spotting nozzle. Impacting air with higher concentration of airborne particles in the desired range increases the collection pace and thus the efficiency or sensitivity of the invented device.

Additionally, some embodiments contain a size selective inlet for preconditioning the air sample by removing particles above a desirable size. A "size-selective inlet" removes particles above a certain size (aerodynamic diameter) from a stream or sample of gas. By "remove" is meant that at a predetermined particle size, 50% of the particles are removed from the gas sample and 50% pass through the size selective inlet. For particles of smaller sizes than the predetermined size, most, or almost all, particles pass through the inlet, while for particles of larger sizes, most, or almost all, particles are removed. The substrate of a size-selective inlet collects the removed particles. In certain preferred embodiments a size selective inlet comprises an inertial impactor. The size of the particles removed is determined, in part, by the velocity of the gas sample as it comes out of the acceleration nozzle. The higher the velocity, the smaller the size of the particles removed. Thus, by selecting the appropriate acceleration nozzle, a predetermined upper size of particles can be removed from a gas sample. In certain embodiments, a size-selective inlet comprises a filter, an elutriator, or any other device capable of removing particles greater than a predetermined size. Preferably, the size selective inlet removes particles above 10 $\mu$m, but may be set to remove particles above other sizes, for example 12 $\mu$m, 15 $\mu$m, 20 $\mu$m, or 25 $\mu$m. In those embodiments where a virtual impactor is present, the size selective inlet may be placed either upstream or downstream of the virtual impactor.

Removal of large airborne particles eliminates potential sources of interference with the analyzer discussed below.

The spotting nozzle directs the air stream towards a collection surface of an impaction plate, thus depositing airborne particles on the collection surface of the impaction plate. The collection surface according to the present invention can be regenerated. Regeneration occurs by the action of a surface regenerator as described below. Regeneration of the collection surface enables continuous and automatic reuse of the device. Thus, unlike other inertial impactors, the present invention does not require a consumable impaction plate.

The impaction plate may take a variety of shapes, but the collection surface is typically flat. In some embodiments, the impaction plate is a disk, i.e. flat, thin, and circular. A disk axis is perpendicularly on the center of the two parallel circular surfaces of the disk. In these embodiments, the collection surface is on one of the two planar parallel surfaces of the disk, preferably at some distance from the center of the disk axis. In other embodiments the impaction plate is a lobed cam. One or several substantially planar surfaces are parallel to the cam axis and function as collection surfaces. A cam shaft along the cam axis is part of the homing sensor as described below.

The impaction plate is preferably made substantially of a homogenous material, although it is possible to embed a collection surface of one material on an impaction plate made of a different material. The plate, or at least its collection surface, is made of a material sufficiently durable to withstand repeated action of the surface regenerator without incurring any damage. Many materials are suitable, including glass, quartz, ceramic, silicon wafers metal or plastic. In addition, coatings can be deposited on one of the above materials to increase the hardness and/or resistance to abrasion. In a preferred embodiment the plate is made entirely of UV transparent material, for example fused silica pure silica, or sapphire (Edmond Scientific).

Figure 3A:
FIG. 3A and FIG. 3B illustrate two embodiments in which outwardly projecting structures are provided on a collection surface to enhance particulate collection.
Figure 3B:
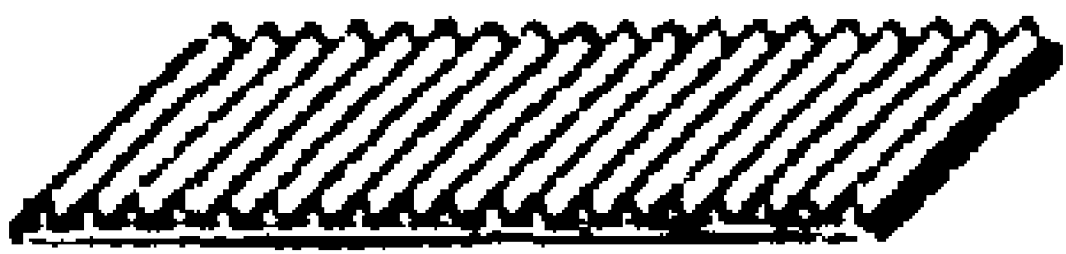

In a preferred embodiment the collection surface is essentially smooth. A smooth surface is preferred as it is easiest to clean by the surface regenerator. On the other hand, particles tend to bounce off smooth surfaces easier, thus decreasing collection efficiency. Consequently, in other embodiments, the collection surface has outwardly projecting structures, such as rods (FIG. 3A) or ribs (FIG. 3B). For example, the surface is micromachined to have pyramid-shaped structures of approximately 1-10 μm in height and width. In these embodiments, particle loss is minimized, but relatively harsher surface regenerators are used.

One function of the impaction plate is to support the collection surface for the accumulation of the sample of airborne particles during impaction. Accordingly, at one point in the cycle of operation of the device, the collection surface is under the spotting nozzle. Typically, the collection surface is horizontal while the spotting nozzle is vertical.

In a preferred embodiment, the impaction plate also functions as part of the homing sensor, as discussed below. The spot on the collection surface is subject to analysis by the analyzer, and the collection surface is regenerated by the surface regenerator (i.e. the surface regenerator cleans the spot from the collection surface).

For example, the impaction plate may less than 150 mm in diameter, and more preferably less than 80 mm in diameter but greater than 20 mm in diamter. The collection surface is preferably less than 25 mm in diameter, and more preferably less than 15 mm but greater than 5 mm in diameter.

Another component of the invented devices is an analyzer for charactering the content of the spot. Analyzers may take a wide variety of forms, depending on the type of airborne particles to be monitored in different applications. For example, analyzers may detect biological particles, specific chemical compounds, or radioactive particles. Detection may be achieved by any one or combination of available techniques, such as mass spectrometry, infrared spectroscopy, fluorescence measurements, or Raman spectroscopy, gamma emission, alpha particle emission, or beta emissions. Monitoring of biological particles is described in some detail below. Useful chemical monitoring may be, for example, of nonvolatile toxic chemicals such as VX chemical warfare agent or mercury containing particulate emitted from coal-fired power plants.

In some embodiments, the invented devices comprise a pre-analysis spot preparation station. At this point the spot is prepared to enhance its characteristics measured by the analyzer. The spot may be combined with compounds that affect measured properties of the airborne particles of interest by squirting a liquid containing the appropriate compound from an inkjet type of device. For example, the liquid may contain matrix solution used in a Matrix Assisted Laser Desorption Ionization (MALDI) mass spectrometer, or a DNA stain that becomes fluorescent when it is bound with DNA, such as ethidium bromide.

It is preferable that any amount of consumable reagents be kept at a minimum to ensure prolonged maintenance free operation of the devices. In one embodiment, the pre-analysis spot preparation station applies a plasma lysis pulse to the spot to expose the contents of any microbes (see for example U.S. Pat. No. 5,989,824)

Another component of the invented devices is a surface regenerator. The purpose of the surface regenerator is to regenerate the surface, i.e. to remove the deposit from the collection surface after analysis, and thus to make the collection surface available for collecting another spot. The surface regenerator must remove substantially all the spot from the collection surface, so prior use of the collection surface does not interfere with analysis of subsequently gathered spots.

In some embodiments, especially where a smooth collection surface is used, a surface regenerator may be felt or cloth pad that is pressed against a moving collection surface as it slides towards the nozzle. By "felt" is meant a porous fibrous structure, typically unwoven, created by interlocking fibers using heat, moisture or pressure. Suitable fibers include, but are not limited to, polyester, polyurethane, polypropylene, and other synthetic and natural fibers. By "cloth" is meant material that is made by weaving, felting, knitting, knotting, or bonding natural or synthetic fibers or filaments. Of course, movement of a pad relative to the collection surface while pressed on it may be achieved by many other known means. Alternatively, a felt or cloth wheel may be used, and a motor spins the wheel when it is in contact with the spot, thus regenerating the collection surface. In other embodiments, the surface regenerator is a brush or blade that remove the spot, for example with a sweeping motion. When the collection surface is not smooth, one or more brushes are desirable, and their sweeping motion may be performed in multiple directions. In yet other embodiments, surface regeneration is achieved by blowing a stream of air at an angle at the spot, i.e. the surface regenerator comprises a nozzle oriented an angle towards the collection surface, which blows a stream of air at high velocity towards the collection surface. In some embodiments, regeneration is aided by electrostatically charging the spot either before or during the action of any regenerator. The collection surface may be temporarily imparted a positive charge, a negative charge, or alternative positive and negative charges. In some embodiments, the regenerator comprises at least in part heaters or lasers capable of transferring energy to the surface spot/collection surface. In some embodiments, multiple regenerators are present and they are either used sequentially in each cycle of the device, or some of them are activated only when necessary, for example in periodic "deep cleaning" cycles, or in response to sensing incomplete regeneration of the collection surface.

In some embodiments, another component of the invented devices is a liquid coating applicator. The function of the liquid coating applicator is to spread a droplet of liquid over the collection surface or a portion thereof before impaction of the air sample. The amount of liquid is typically minuscule, and so essentially all of the applied liquid evaporates during the subsequent air impaction with the collection surface. The purpose of the liquid is to reduce particle bounce from the collection surface, at least at the initial stages of gathering the spot. Thus, a spot nucleus forms which reduces particle bounce during the remaining time of acquisition of the spot and improving collection efficiency. In these embodiments, a consumable (the liquid) is necessary, but it is used up in minute amounts. A relatively small liquid reservoir thus can contain and make available liquid for a very large number of cycles. For example, a 500 ml reservoir might suffice for 10,000 cycles. Accordingly, replenishing the consumable is required quite rarely.

Any liquid capable of trapping impacting particles may be used, such as water, alcohols such as ethanol or methanol, glycerol, a mineral oil, or medium weight hydrocarbons such as octane. It is important that the liquid does not affect the collected spot so as to interfere with its subsequent analysis.

The amount of liquid necessary may vary with the nature of the liquid and other features and dimensions of the device. Usually, the volume of liquid for each application is from 0.5 μl to 50 μl, and may be, for example, 0.5, 1, 2, 3, 4, 5, 6, 7, 8, 9, 10, 15, 20, 25, 30, 35, 40, 45, or 50 μl. It is preferred that an identical volume of liquid is applied in each cycle of operation.

Any device capable of spreading a liquid droplet on a surface may be used as an applicator in the present invention. In a preferred embodiment, the applicator is a felt tip pen.

Another component of the invented devices is a homing sensor. The function of the homing sensor is to move the collection surface between the spotting nozzle, the analyzer, the regenerator, and, in some embodiments, the liquid coating applicator. Thus, each component of the invented device can perform their respective function on the collection surface.

The homing sensor is a mechanical device that alters the position of the collection surface with respect to the other components. Thus, the homing sensor is not a sensor in the usual meaning of the term, although in some embodiments one or more sensors may be present and capable to detect and communicate the position of the collection surface within the functional cycle. Many types of mechanisms can be used as homing sensors. In one embodiment, the spotting nozzle, analyzer, regenerator, and liquid coating applicator if present, have fixed positions. The collection surface is on a face of a disk. On the opposite face a shaft is attached down the axis of the disk, the shaft being coupled to a prime mover. The disk can thus be rotated at predetermined angles to position the collection surface sequentially for each component. In another embodiment, the impaction plate is a lobed cam having a shaft. There is at least one planar collection surface essentially parallel to the shaft. In these embodiments, the homing sensor comprises the impaction plate, shaft and prime mover. Those of skill in the art will recognize that other mechanical structures can accomplish the function of the homing sensor. Thus, the collection surface may be moved substantially linearly, or the collection surface may be retained in a fixed location while other components are repositioned with respect to the collection surface. Accordingly, any known means of translocationg the collection surface relative to other components may be used.

In operation, an air stream is pulled through the air inlet of the spotting nozzle. The air stream is a sample of environmental air. The sample is pre-concentrated in some embodiments by the action of a virtual impactor upstream of the air inlet of the spotting nozzle, so that the air stream is enriched in particles of the 1-10 μm range. The air sample is also preconditioned in some embodiments by the action of a size selective inlet upstream of the spotting nozzle to eliminate particles above a desired size, such as 10 μm, to improve the desired air composition.

The air stream emerging from the spotting nozzle impacts on the collection surface of the impaction plate. As a result, a spot forms that consists mainly of particles in the desired size range, which is preferably of an aerodynamic diameter of 1-10 μm. The collection efficiency of the collection surface may be low as long as it is roughly consistent for different particle concentrations. By collection efficiency is meant the proportion of particles in the desired size range in the air sample that is trapped on the collection surface as a result of impaction.

In some embodiments, prior to impaction of the air stream by the spotting nozzle, the collection surface of the impaction plate is coated with a liquid by the action of a liquid coating applicator. The liquid coating improves the collection efficiency of the collection surface.

The position of the collection surface relative to other components of the invented devices changes through the action of a homing sensor. Thus, the homing sensor automatically positions the collection surface sequentially from the liquid coating applicator, if one is present, to the spotting nozzle, to the analyzer, and to the regenerator or regenerators. In some embodiments, the homing sensor may be able to vary the order of repositioning the collection surface in certain circumstances. For example, the homing sensor could be able to move the collection surface from the regenerator to the analyzer if or when it is desirable to ensure proper regeneration of the collection surface.

After a spot accumulates on the collection surface by the action of the spotting nozzle, movement of air through the spotting nozzle usually ceases and the collection surface with the spot moves to the analyzer. In some embodiments, a first step at this stage is preparing the sample for analysis at the pre-analysis spot preparation station. The analyzer then detects the presence and/or measures the concentration specific airborne particles or constituents thereof.

Following analysis, the collection surface is moved by the homing sensor to the surface regenerator, which acts to clean the collection surface and thus regenerate it for another cycle of operation. The regenerator may act by one or several mechanisms to regenerate the collection surface. Thus, the regenerator could act by a mechanical brushing or wiping of the surface, by blowing an air stream at high velocity towards the spot, preferably at an angle, and/or by electrostatically charging the spot. Following the action of the regenerator, the collection surface is used again in another cycle of collection, analysis, and regeneration. The number of cycles that a device can perform automatically without any need for service is very large, preferably in the thousands.

In another aspect, the present invention relates to methods for continuously monitoring airborne particles (see FIG. 4). The airborne particles being monitored are preferably biological particles, although specific chemicals or radioisotopes may also be monitored, and monitoring implies detection of their presence, their concentration and/or possibly their nature. Continuous detection refers to repeated sampling of environmental air. By continuous it is not meant that necessarily air samples are uninterruptedly being evaluated, but rather air samples may be evaluated at repeated time intervals. Thus, detection of airborne particles occurs in cycles that comprise at least some identical steps. The main steps of each cycle are immobilizing airborne particles on a collection surface, analyzing the immobilized airborne particles, and regenerating the collection surface. Additional steps are performed in some embodiments.

A step according to the present methods is depositing airborne particles on a collection surface (440). At this step, airborne particles are extracted from ambient air. Any known extraction methods may be used if it results in depositing airborne particles on a collection surface. In a preferred embodiment, however, depositing airborne particles is achieved by inertial impaction.

As a result of depositing airborne particles, a spot forms on the collection surface. The spot contains extracted or immobilized airborne particles from the ambient air sample. However, not every particle in the original ambient air sample needs to be deposited on the collection surface at this step. It is envisioned that particles of a desirable size range may be enriched in the spot. In fact, in some embodiments particles of undesirable size ranges may be actively excluded. The precise size range differs as required by specific applications. In preferred embodiments, particles of 1-10 μm comprise the desirable size range. Particles in this size range may be inhaled and may include dangerous biologicals.

In some embodiments, airborne particles of a desirable size range are concentrated in a step preceding depositing airborne particles on the collection surface (420). Concentration may be achieved, for example, by the action of a virtual impactor. This concentration of particles allows quick sampling of large volumes of air, which decreases the time required for performing each cycle of the invented methods, and therefore improves the performance and ultimately the safety of the air.

In some embodiments the sampled air is preconditioned prior to depositing airborne particles on the collection surface (410). By preconditioned it is meant that particles greater than a desirable size are removed from the sample. This may be accomplished with a size selective inlet as discussed above. Particles greater than the desired size range may be first removed from the air, and thus such particles do not end up in the spot. Consequently, they cannot interfere with the analysis of the spot described below. Preconditioning may remove, for example, particles greater than 10 μm, but may remove only particles greater than other sizes, for example 5 μm, 7 μm, 8 μm, 12 μm, 15 μm, 20 μm, or 25 μm. In some embodiments, both preconditioning and concentration are performed prior to depositing particles on the surface.

In some embodiments, another step that may be performed prior to depositing airborne particles is moistening the collection surface (430). Many types of liquids may be used to moisten the collection surface including glycerol, alcohols, or medium weight hydrocarbons, such as octane, as mentioned above in describing the liquid coating applicator. The precise volume of liquid used in each cycle depends on several different variables, and may be about 0.5, 1, 2, 3, 4, 5, 6, 7, 8, 9, 10, 15, 20, 25, 30, 35, 40, 45, or 50 μl.

Another step of the invented methods comprises analysis of the spot (450). The type of analysis performed depends on the nature of the particles to be monitored. Appropriate analyses of spots for biological materials are described in some detail below. Chemical, radiological, or any other type of analysis may be performed according to any known suitable test. In some embodiments, analyzing comprises an optional step of pre-treating the spot so as to enhance the measured signal. Thus, pre-treating may comprise adding to the spot a liquid comprising an analysis-enhancing compound. In some embodiments where analyzing is accomplished by MALDI mass spectrometry, pre-treating may be performed by plasma lysing.

Another step of the invented methods comprises regenerating the collection surface (460). The precise nature of the physical act that accomplishes regeneration depends on many variables such as the application that employs the methods, the expected average air characteristics, or the type of collection surface used. Regeneration may be achieved by any one or combination of steps. For example, in some embodiments, regeneration is accomplished by pressing a felt pad against the collection surface and moving the felt pad over the collection surface. In other embodiments a felt wheel is rotated while pressed against the collection surface. In other embodiments the collection surface is electrostatically charged as part of the regeneration step. In other embodiments regeneration is accomplished by brushing the collection surface with a brush. In other embodiments regeneration is accomplished by blowing an air jet at high velocity towards the collection surface. In other embodiments, regeneration is accomplished by scraping or wiping the collection surface with a blade. Regenerating the surface may be achieved by one or more acts. When more than one act is used, the acts may be similar or identical, or they may be different. In some embodiments, specific regeneration acts are not necessarily performed in each cycle.

In some embodiments all the cycles of the invented methods are identical. In other embodiments, some cycles may comprise different steps from other cycles.

In some embodiments, the invented methods in at least a subset of cycles comprise verifying the regeneration of the surface (470). Accordingly, the collection surface is analyzed again after regeneration. This analysis may be performed essentially by the same process or test that was used for analyzing the spot. Thus a background signal level is obtained for the regenerated surface. The background signal level is then compared to predetermined criteria. If the background level is found to be higher than desirable, regeneration and verification is repeated until the background signal level meets predetermined criteria. Alternatively, a test may be employed in assessing if regeneration was acceptably accomplished that is different from the sample analysis test.

Each cycle of the invented methods may be considered to start with depositing airborne particles on the collection surface to form the spot (440). In those embodiments that comprise preconditioning (410) and/or concentrating (420) the air sample from which particles are extracted, the additional step(s) can occur essentially simultaneously with the step of depositing particles on the surface. In those embodiments where the methods comprise moistening the collection surface (430), this step may be seen as the first step of each cycle. Of course, given the cyclical nature of the invented methods, the selection of any step as the first is arbitrary.

After completion of the depositing step, each cycle comprises the step of analyzing the spot present on the collection surface (450). During analysis, data regarding properties of the sample is gathered and transmitted. This way, the methods are useful in acquiring and conveying information about the presence and quantity of airborne particles of interest such as biological particles.

After analysis the next step is regenerating the collection surface (460). The surface is regenerated by any one or more feasible means. In some embodiments, proper regeneration is verified in at least a subset of cycles (470). Thus, the collection surface may be re-analyzed.

After regeneration, the next cycle proceeds with depositing airborne particles from another air sample, which is preceded in some embodiments by moistening the collection surface.

In another aspect, the present invention relates generally to devices useful for monitoring airborne biological particles. The devices can analyze the content of extracted particles deposited as a spot on a collection surface, preferably a regenerative. By regenerative collection surface it is meant a collection surface on which a spot of airborne particles can be deposited or immobilized for a period of time, and then the spot can be removed thus regenerating or refreshing the surface. The regenerated collection surface has similar characteristics to the collection surface prior to the previous spot immobilization. The surface refreshing need not necessarily achieve virtually identical characteristics. Rather, the surface must be sufficiently regenerated that the next signal resulting from any residue will be insignificant relative to the signal resulting by the sample spot. Thus, the regenerative collection surface can be used in numerous similar cycles of spot immobilization and regeneration. Regenerative collection surfaces are described in more detail above.

The devices also comprise in some embodiments the means of extracting particles from ambient air and depositing or immobilizing them on the surface, such as an inertial impactor. Thus, the airborne particles are immobilized on a collection surface as a spot.

The invented devices comprise a detector that is capable of analyzing the content of the spot. The detector determines the presence of a property inherent to biological particles, thus determining the presence and/or concentration of airborne biological materials, which may include biohazards. Biological materials may be bacteria and/or viral and/or protein aggregates. As bacteria can clump together, the term "particle" as used herein is understood to include inert particles, a single biological entity or biological (typically 0.5-2 µm), or an aggregate of these small biologicals (aggregates of about 2-10 µm).

Any known property inherent to biological particles or to specific subsets of biological particles may be subject to analysis. There are many examples of such properties, sometimes called biological signatures, and they may be detected by optical or non-optical methods. Examples of known useful properties include fluorescence that may be characterized by single or multi-wavelength excitation and/or emission and/or fluorescence lifetime, IR absorption, Raman scattering, mass specters, or terahertz specters. Examples of useful analytical techniques include fluorescence spectroscopy, Fourier-transform infrared spectroscopy, laser induced breakdown spectroscopy or aerosol time-of-flight mass spectrometry, MALDI mass spectrometry, surface enhanced Raman spectroscopy, planar optical waveguide sensing by evanescent waves, or terahertz spectroscopy.

During analysis, the spot produces a signal that is measured by any suitable detection means. Where the signal is detected optically, detection may be accomplished using any optical detector that is compatible with the spectroscopic properties of the produced signal. The assay may involve an increase in an optical signal or a decrease. The optical signal may be based on any of a variety of optical principles, including fluorescence, elastic scattering, light absorbance, polarization, circular dichroism, optical rotation, Raman scattering, and light scattering. Preferably, the optical signal is based on the intrinsic fluorescence of biological particles.

In general, the optical signal to be detected will involve absorbance or emission of light having a wavelength between about 180 nm (ultraviolet) and about 50 µm (far infrared). More typically, the wavelength is between about 200 nm (ultraviolet) and about 800 nm (near infrared). A variety of detection apparatus for measuring light having such wavelengths are known in the art, and will typically involve the use of light filters, photomultipliers, diode-based detectors, and/or charge-coupled detectors (CCD), for example. The optical signal produced by a spot may be based on detection of light having one or more selected wavelengths with defined band-widths (e.g., 500 nm+/−0.5 nm). Alternatively, the optical signal may be based on the shape or profile of emitted or absorbed light in a selected wavelength range. This profile can measured by an array of narrow bandwidth sensors or with a spectral photometer (such as that sold by Ocean Optics, Inc.) The signals may be recorded with the aid of a computer.

In preferred embodiments the analyzer is a fluorescence detector, which comprises an excitation light. source for stimulating the fluorophores on the collection surface and a fluorescence photosensor for measuring the resulting emissions from the spot. The optical signals produced by individual spots may be measured sequentially by iteratively interrogating the deposit with light of different wavelengths and/or measuring different emission characteristics.

In some embodiments, the optical signal measurement will involve light having at least two distinctive wavelengths in order to include an internal control. For example, a first wavelength is used to determine the presence or concentration of biological materials, and a second wavelength is used to determine the presence or concentration of non-biological materials that may interfere with the reading at the first wavelength. An aberration or absence of the signal for the second wavelength is an indication that the sample was improperly prepared, the estimate of concentration of biological particles is unreliable in that cycle, nonbiological airborne materials are present and affect the fluorescence expected from biological particles in the sample, or the analyzer is malfunctioning.

Biological materials are known to contain autofluorescent materials. For example, fluorophores include the aromatic amino acids tryptophan, tyrosine, and phnylalanine, nicotinamide adenine dinucleotide compounds (NADH and NADPH), flavins, and chlorophylls. In addition, cultured bacteria are known to have characteristic fluorescence features distinguishable from wild bacteria. This property may be employed in the design of the biological alarm as biological weapons are typically produced in cultures.

In some embodiments, improved discrimination between biological particles and other non-biological particles is possible by incorporating several excitation wavelengths in sequential manner, thereby interrogating each sample spot multiples times.

Measuring intrinsic fluorescence of particles trapped in a spot requires comparatively less sophisticated equipment than that necessary for similar measurements of particles in an airborne state. Fluorescence emissions are typically higher due to the presence of concentrated fluorophores. Excitation can thus be performed with less powerful sources, for example, depending on the embodiment with typical electric-arc lamp, LED or laser diodes, although any other types of lasers may also be used. For example, laser diodes or LEDs suitable for some embodiments may be obtained from Nichia Corporation, Tokushima, JAPAN. In addition, excitation for longer time periods is possible. In some embodiments, fluorescence spectra can be collected, while in others only peak fluorescence emission is of interest. Additionally, several autofluorescence characteristics can be determined for each spot. For example, as detailed below, fluorescence emitted in response to excitation at about 266 nm, 340 nm, 360 nm and/or 400 nm, may be measured for each spot.

Fluorescence detectors comprise an excitation light source, such as an UV light source, and a fluorescence photosensor for measuring light emitted from a sample in response to excitation. Any light detector can be used as a detection device. Three common detectors are (1) photomultiplier tubes (PMT), (2) avalanche photo-diodes; and (3) solid-state silicon photo diodes. Focusing the light may be important depending on the type of detector that is used. For example, avalanche photo-diodes have relatively small detection surfaces. Consequently, when using avalanche photo-diodes, it is preferable to focus the light so as to direct the light to the avalanche photo-diode's detection surface. Focusing the fluorescence signal to a small sensor is preferable because it will becomes more likely for stray light to miss the sensor. In some cases, smaller sensors have less noise than sensors with larger active areas.

Figure 2:
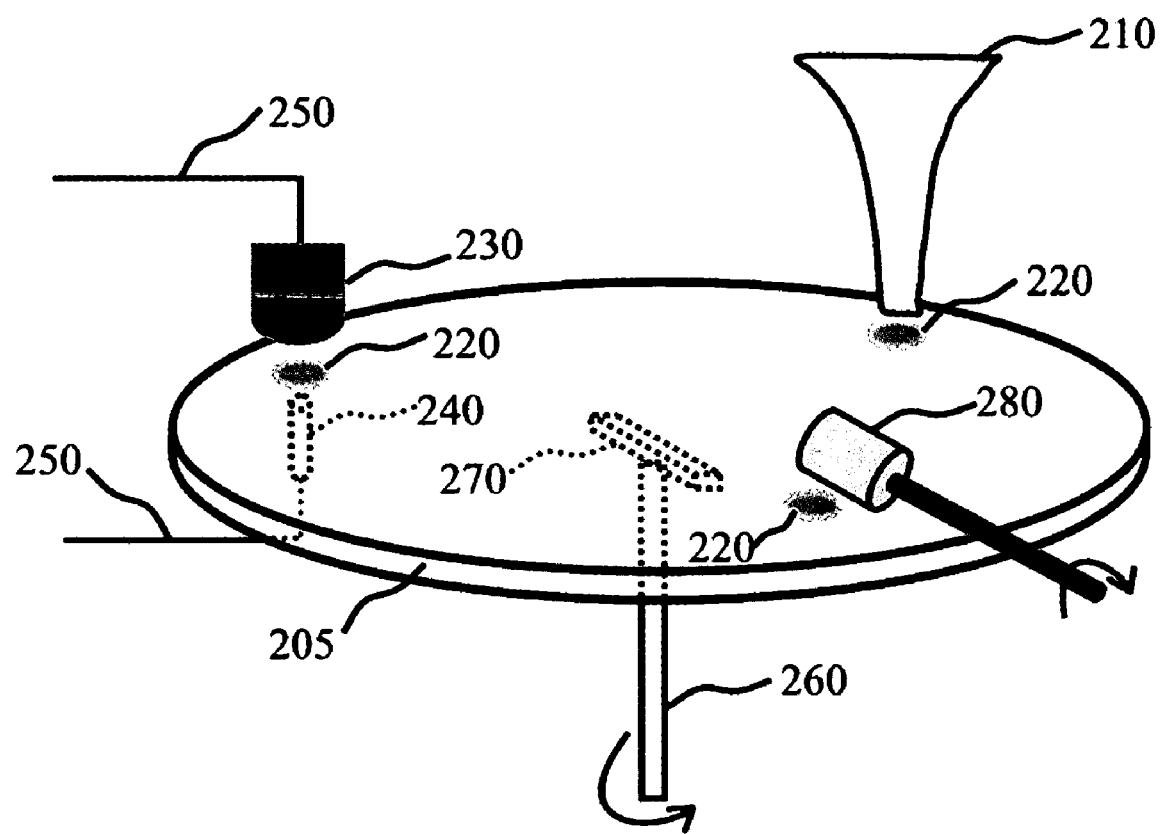
FIG. 2 is a diagram of several components present in various embodiments of the present invention, namely an impaction plate (205) with a collection surface on which a deposit forms (220), a spotting nozzle (210), an analyzer comprising a fluorescence photosensor (230) and an excitation light source (240) coupled by wires (250), a shaft (260) mounted to the impaction plate (205) by a bracket (270) and a regenerator (280). Three collection surfaces/spots are drawn only for illustration; a single collection surface suffices in most embodiments.

In one embodiment the excitation light source is positioned underneath a horizontal UV transparent impact plate, and the emission sensor is positioned above the plate, as is the collection surface (see FIG. 2). For example, the impaction plate may be shaped as a disk or may otherwise be planar. Accordingly, the impaction plate has a collection surface side, on which the spot forms, and a side opposite to the collection surface side, which may be called the interrogation side. In some embodiments, the impaction plate is made at least in part of a material substantially transparent to ultraviolet radiation. In these embodiments the spot is collected on a UV transparent collection surface. In these embodiments, the impaction plate allows components of UV-based detectors, such as an excitation light source and fluorescence photodetector, to be placed on the two opposite sides of the impaction plate. Thus, the excitation light source may be placed on the interrogation side and the fluorescence photosensor is placed on the collection surface side.

Figure 5:
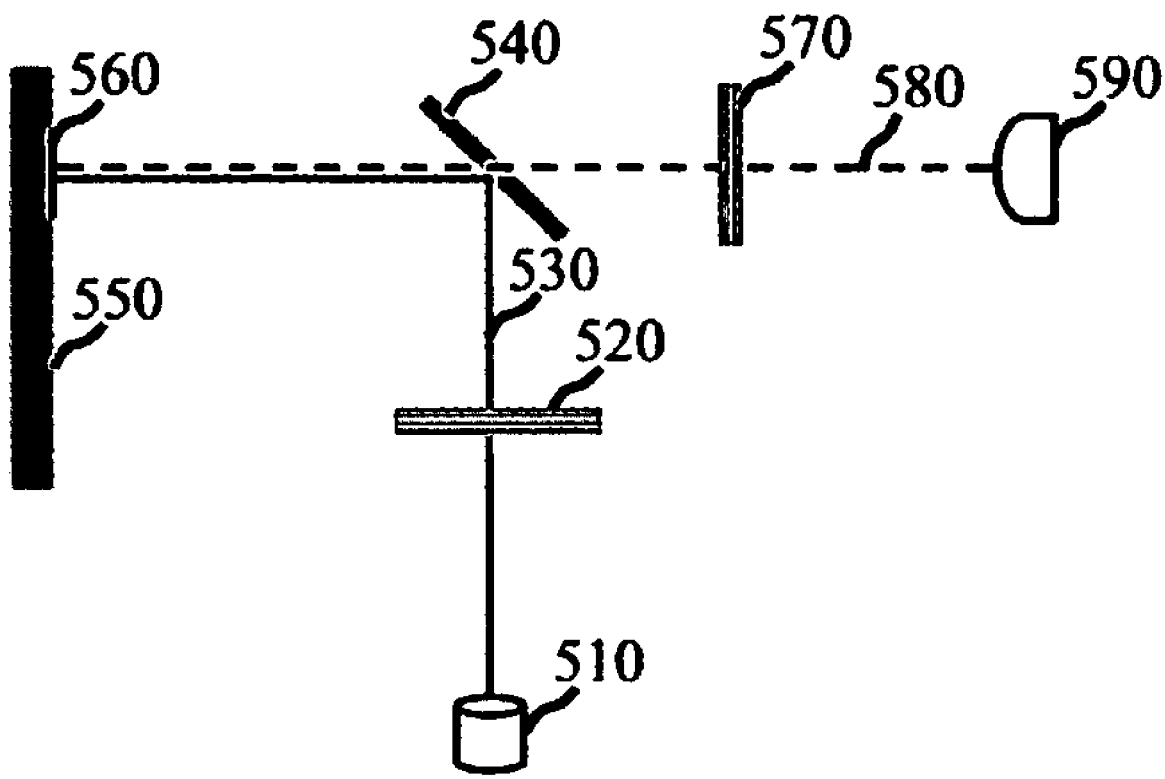
FIG. 5 illustrates an arrangement of the components of a fluorescence detector. A UV LED 510 emits an excitatory light 530 that passes through excitation filter 520. A dichroic mirror reflects the excitatory UV light, which then reaches the sample spot 560 on a regenerative surface 550. Fluorescent light 580 in the visible part of the spectrum passes through the dichroic mirror 540 and an emission filter 570 until it reaches the photodiode detector 590.
Figure 6:
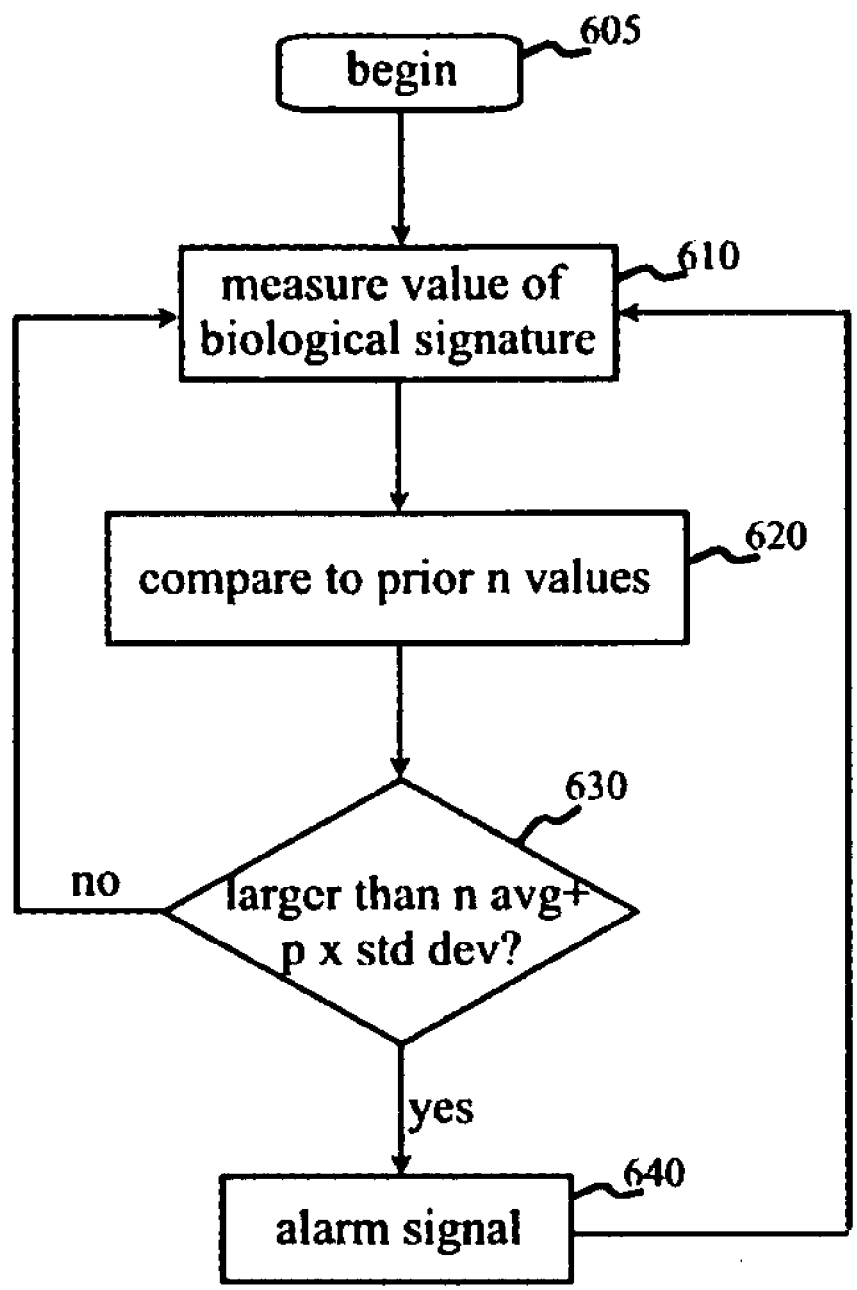
FIG. 6 is a flow diagram of the signal processing for determining the presence unusually high concentrations of airborne biological particles.

In other embodiments, the excitation light source and the photosensor are both placed on the same side. The fluorescence is separated from the excitation light with optical filters. One example of such an embodiment is illustrated in FIG. 5. An UV LED (510) emits light (530) of an excitatory wavelength, which may be in the range of about 340 to 380 nm. The excitatory radiation is reflected by a dichroic mirror (540) towards the spot (560) deposited on a collection surface. The dichroic mirror substantially reflects excitatory radiation and is substantially transparent to fluorescence radiation, in this case in the visible part of the spectrum (see FIG. 7 for the transmission characteristics of the dichroic mirror, excitation and emission filters). Fluorescence emissions (580) pass through the dichroic mirror (540) and an emission filter (570), then reaching the photodiode (590). Focusing lenses are not shown in the drawing.

Those of skill in the art appreciate that many variables can be optimized, for example angles between the emitter and sensor may be adjusted for maximum signal to noise ratio, filters may be used to reduce or eliminate undesirable wavelengths, or an excitation laser beam may be pulsed and the receiver coupled to the photodetector may be gated to respond in a delayed manner during a short period following each laser illumination pulse, so as to discriminate against false ambient illumination.

The spot is immobilized for an amount of time suitable for multiple analytical measurements. Thus, the intrinsic fluorescence properties of the deposit may be analyzed sequentially at different excitation wavelengths. For example, excitation wavelengths may be of about 266 nm, 340 nm, and/or 400 nm. Excitation at different wavelengths is desirable in some embodiments, as it is expected that non-biological materials also autofluoresce thus interfering with accurate quantification of biological materials present in the spot. Furthermore, it may be possible to distinguish between various classes of biologicals by measuring the fluorescence signature and comparing that signature to known signatures for specific classes of biologicals. For example, by using multiple wavelengths of excitation light and measuring the fluorescence emission spectra over at least several ranges of wavelengths, it may be possible to differentiate bacteria, viruses, bacterial spores, mold spores, and fungi. Within each class, it may be possible to identify cultured from naturally occurring specimens. Thus, a better characterization of biological materials is possible through characterization of fluorescence of airborne particles in response to different excitation wavelengths.

In another embodiment, a particle counter may be used in parallel with a sensor based on a regenerative surface to assist in the characterization of the biologicals. Particle counters use light scattering as particles pass through a beam of light to measure the density particles in air. Some particle counters are also capable of determining the size of each particle. Some particle counters are capable of assessing characteristics of the particle shape based on the particle's light scattering properties. If a particle counter is capable of measuring either or both the size and the shape of many particles in a short period of time, then a dynamic measure of either or both of the particle size distribution and particle shape distribution in air coincident with the particles being analyzed by the sensor based on a regenerative surface. Thus, a better characterization of biological materials is possible through characterization of fluorescence, combined with particle counts broken down by either or both of size and shape.

In another embodiment, two detection methods can be used in sequential combination within a sensor based regenerative surface air sampler to assist in the characterization of the biologicals. For example, after the sample spot is created, the spot may be analyzed sequentially by fluorescence and then by Raman. A Raman sensor may be capable to differentiate various species or genii within a specific class of microbes. Such a combination of sensors would allow for greater confidence in the need to indicate an alarm in response to a particular sample spot.

One useful excitation wavelength is 266 nm, which excites amino acids tryptophan and tyrosine, which have peak emissions around 340 nm and 310 nm respectively. 266 nm UV light also excites NADH and riboflavin, which have emission peaks from airborne particles around 450 nm and 560 nm respectively. In addition to 266 nm, it is feasible to use other close wavelengths, for example 220, 225, 230, 235, 240, 245, 250, 255, 260, 265, 270, 275, 280, 285, 290, or 295 nm. While nonbiological airborne particles within the size range of interest also fluoresce in response to 266 nm UV light, the fluorescence spectra of tryptophan and tyrosine-containing particles exhibit characteristic intensity peaks (between about 310-350 nm; see Pan et al., Field Analytical Chemistry and Technology 3:221-239, 1999). These characteristic peaks can be used to quantitatively distinguish the amount of biological materials relative to non-biological particles which typically have broad emissions spectra. For example, emissions at the expected peak intensity of about 340 may be normalized to emissions at other spectral regions, for example around about 400 nm and/or 500 nm.

Another useful excitation wavelength is about 340 nm. Two related fluorescent coenzymes or biomolecules are found in all living cells: nicotinamide adenine dinucleotide phosphate (NADP) and nicotinamide adenine dinucleotide (NAD). They are essential for cellular metabolism, and therefore their fluorescence can serve to monitor the presence and/or concentration of airborne bacteria. In other words, these measurements are especially suitable for determining the presence and/or concentration of viable airborne cells, such as bacterial cells. The fluorescence excitation and emission wavelengths of NADH are well separated, which facilitates detection. The excitation wavelength of NADH/NAD(P)H is centered at 340 nm in the near ultraviolet spectrum, and their fluorescent emission wavelength extends from 400 to 540 nm. Thus, a desirable excitation wavelength is about 340 nm, but it is feasible to use other close wavelengths, for example 320, 325, 330, 335, 345, 350, 351, 355, 360, 370, 375, or 380 nm.

Riboflavin, a flavonoid, has fluorescent wavebands that partially overlap those of NADH, so it may also be detected by a system designed for NADH, or it may be detected in separate measurements. Riboflavin, exhibits peak excitation at approximately 400 nm, with characteristic emission between 475 nm and 580 nm (Li et al. in Monitoring Cell Concentration and Activity by Multiple Excitation Fluorometry, Biotechnol. Prog., 1991, p: 21-27). The presence of both NADH and riboflavin are characteristic of viable bacteria in an air medium. Thus, autofluorescence in response to these wavelengths of excitation can indicate the presence of viable bacteria or cells (see, for example, U.S. Pat. No. 5,895,922, and U.S. patent application Ser. No. 09/993,448). The longer excitation wavelength of less energy also makes it less likely for fluorescence to occur in a wide group of non-biological particles that would interfere with the measurements.

As mentioned above, the detector produces signals, typically electrical signals, which are related to the biological signature detected. The signals are conveyed to a receiver, which may then relay the signals for further processing. The signals typically reach a processor, which may be a computer or a Neuron Chip® as described in more detail below. The processor is capable to process or interpret the signals and thus establish or gauge the concentration of biological particles in the spot. Such signal processing may be performed according to the methods outlined below. Consequently, the processor is capable to establish when the concentration of biological particles in the spot exceeds a predetermined value. In such a case, the processor outputs an alarm signal that alerts users of the presence of potentially harmful airborne biological particles.

In one embodiment, a photodetector is connected to current-to-voltage converter if the photodetector outputs a current proportional to the incident light. This voltage may need amplification to give an output signal in the 0-5 volt range. The signal may require filtration to reduce the noise, thereby increasing the signal to noise ratio. The signal is then fed to an analog-to-digital converter. The digital signal is then read and processed by a microprocessor.

In yet another aspect, the present invention relates to methods of detecting specific airborne particles or monitoring concentrations of airborne biological materials. The methods comprise a plurality of steps, which may be repeated cyclically to ensure continuous monitoring of environmental air.

One step according to the invented methods is depositing airborne particles on a regenerative collection surface to form a spot, which may be accomplished by inertial impaction.

Another step comprises measuring a biological signature present in the spot (FIG. 6). Any biological signature and its corresponding measurement known in the art, including those discussed in some detail above, may be utilized at this step. Consequently this measurement indicates the concentration of airborne biological particles. Each measurement performed on a spot deposited on a regenerative surface provides a value of the concentration of airborne biological particles (610).

Values from a defined number of preceding measurements may be stored temporarily. They can be used in calculating the average value and the standard deviation from prior measurements. Any number of measurements, for example 3, 4, 5, 6, 7, 8, 9, 10 or more, may be used in calculating the average and standard deviation. The number of preceding measurements (n) used in calculations is typically constant.

The value of the last measurement is then compared to the calculated average of preceding measurements to determine if the present value exceeds the average to a significant extent (620). The standard deviation from the prior measurements can be used to establish if the present value is abnormally high, i.e. if the present value exceeds the average to a significant extent. Thus, the present value may be compared to the average value plus a preset number (p) multiplied by the standard deviation (630). For example, the preset number may be between 2 and 8, although it may be set at different levels depending on specific operating conditions of the invented methods. If the present value does exceed the average value to a significant extent, then the processor outputs an alarm signal (640). Other algorithms may also be suitable and by be preferable for specific applications.

Another step is regenerating the collection surface. Then, the processor proceeds to analyze a newly obtained present value from another spot.

In other aspects, the present invention provides sensors, sensor systems and networks based on regenerative surface air samplers. Integrated in various applications, the invented devices and systems are useful for monitoring and controlling air quality, as well as warning promptly of the presence of potentially noxious airborne hazards. Sensors based on regenerative surface air samplers can be adapted to monitor the presence of any airborne hazard. For example, biological, chemical, or radiological sensors can be used to continuously detect the presence of respective particles in the ambient air.

By sensors it is meant devices that are responsive to changes in the quantity to be measured. As used herein sensors may encompass transducers that convert measurements into electrical signals.

Sensors according to the present invention are desirable in a large number of civilian or military contexts. They are especially useful in densely populated and possibly closed areas. For example, they are desirable in buildings or public facilities like stadiums or auditoriums where a large number of people may get simultaneously exposed to airborne hazards. They may be mounted on walls or ceilings, and may be especially useful in air ducts and air plenums, at entrance or delivery points. As such, sensors may interact with HVAC systems, or may be part of HVAC systems. The present sensors may also be useful in any vehicles such as airplanes or cruise ships.

Sensors based on regenerative surface air samplers may be embodied as various types of devices. As those of skill in the art will appreciate, devices attached to sensors may have various types of processing capabilities. Dumb sensors may simply generate analog or digital uncalibrated or calibrated outputs. Smart sensors may fuse or correlate different readings to send a number of different types of alerts, or have communication capabilities and can be programmed to send raw data and/or sets of alerts. Intelligent sensors can additionally reason about how to investigate and resolve their own alerts. The sensors communicate their signals through a communication interface. In simpler embodiments, the sensors may merely issue a local audio or visual signal. In other embodiments, however, the sensors communicate information through the communication interface to one or more distant locations. The communication interface may be simply a transmitter in some cases, such as with dumb sensors. In other embodiments the communication interface is a transceiver, i.e. a device that is both a transmitter and a receiver for a communications channel.

Signals from and to sensors may be communicated by any known feasible means. As such, signals are communicated through wired or wireless connections. Examples of wired connections include twisted pair, coaxial, power lines, or fiber optic cables. Examples of wireless connections include radio frequency (RF), infrared (IR) communication means. For example, in some embodiments the transceiver communicates via an RF link to an RF link network.

In many embodiments a controller is coupled to the sensor. In some embodiments, the controller is a programmed personal computer or other computer with processor, memory and I/O devices. In some embodiments the controller is a Neuron® chip, a system-on-chip microcontroller used with LonTalk®, LonWorks® communications protocol referred to below. Different chip versions share the same basic features in various combinations: processor cores, memory, communications, and I/O, as well as sensors, actuators, and transceivers. The Neuron® chip is actually three, 8-bit inline processors in one. Two of the processors execute the LONWORKS protocol referred to below, and the third is for the device's application. The chip is, therefore, both a network communications processor and an application processor. Typically, the controller is also coupled to a transceiver. In some embodiments, the function of the controller may be performed by more than one computer or controller, which may be coupled through a network. The controller may incorporate software or firmware used to operate sensors based on regenerative surfaces. The methods of operation embodied in the software or firmware may be substantially similar to the methods of detecting biological particles disclosed herein. The controller may operate or integrate information from other system components as described below.

Signals from the communication interface are typically communicated over a network or system that may be a computer data network, but is more typically a control network, such as a building automation network. There are many examples of systems in which sensors based on regenerative surface air samplers may be integrated. One such system is the CEBus system, which has been made an EIA standard, known as the EIA 600 standard, which was originally developed by Intellon Corp. A second system is the LonWorks system commercially available from and developed by Echelon Corp, San Jose, Calif. Both the CEBus and LonWorks systems specify physical and link layer means for communicating over a variety of different media including power line, coaxial cable, fiber optic cable, radio frequency (RF), infrared (IR) and twisted pair cable. While the sensors may be adapted to communicate by a variety of means, it is preferable that the sensors communicate to a local operating network using a standard protocol, such as the BACnet (ISO standard 16484-5) protocol or the LonTalk® (also known as the ANSI/EIA 709.1 Control Networking Standard) protocol, CEBus, X10 or CAN. Sensors based on regenerative surfaces may also be integrated into any other sensor network, such as the one described in U.S. patent application Ser. No. 10/021,898.

In some embodiments the controller is coupled to at least one actuator and configured to operate at least one air management component in response to information received from the sensor. Thus, in response to a potential hazard indicated by the sensor, the controller may turn on one or more components. It may be useful to activate different types of system components in such situations. The components may be loosely categorized as air analysis devices, air control devices, or self-diagnostic devices. Depending on the configuration of the system, the actuated devices may be near or far from the sensor that issued the original alert, and they may be located indoors or outdoors. The controller may also be communicatively coupled to the air management component, and thus it may be able to receive and integrate information additional to that received from sensors based on regenerative surfaces. Evacuation alarms may be triggered based solely on information from a sensor based on a regenerative surface, or may be triggered based on additional information also available.

Air analysis devices may be any devices known in the art that would be useful in analyzing the composition of air. Examples of suitable devices include a light detection and ranging (Lidar) system, an aerodynamic particle sizer, a mass spectrometer to detect chemicals present in the threat, sample capture and archival devices (as in U.S. patent application Ser. No. 10/366,595) or specific antibody or PCR based sensing to precisely identify agents in the threat. Use of specific sensors may minimize the impact of false alarms. They also provide information valuable for treatment of affected personnel. Sensors of this type perform DNA analysis using the PCR technology, and antibody analysis using antibody-based assays.

Air control devices control the flow of air, such as by operating dampers of an HVAC system. Thus an HVAC system can be used to control the flow of air within a building in response to a threat. If the threat is exterior to the building, air is stopped from entering the building, or air is taken in through alternate air intakes that do not appear to be affected by the threat. If the threat is from within the building, its location can be identified, and air exhausted from the threatened area, while providing fresh, unaffected air to the non affected areas of the building. Other examples of air control devices include UV lights, heat or microwave, HEPA filters, and corona based disinfection, chemical foggers, thermo or photocatalytic filters, or carbon filters.

In some embodiments, sensors based on regenerative surfaces have self-diagnostic capabilities. Operation of various components the regenerative surface sensor may be itself monitored by one or more sensors, which may be coupled to the controller. The controller may turn on a self-diagnostic program either periodically or as part of a response to an alarm by the sensor.

Because sensors based on regenerative surfaces are desirably active in emergency situations, in some embodiments they include a battery backup. Thus, while the sensors are routinely powered from a regular alternative current outlet, they may have a battery backup to be used during power outages.

Data on the control network may be transmitted or accessible to a large number of interested persons, or organizations, or systems, such as facility managers, fire departments or law enforcement agencies, and/or building security systems.

In operation, sensors based on regenerative surfaces operate virtually continuously in a sampling mode. When they detect a high probability of presence of airborne hazards, they issue an alert signal, which may be communicated locally and/or remotely. At the same time, depending on the specific embodiment, the sensors may activate a self-diagnosis program, activate specific sensors, and/or initiate prophylactic measures such as operate air duct dampers to contain the contamination, or increase intake of outside air by the HVAC system.

System components other than sensors based on regenerative surfaces usually operate in a standby mode to conserve power and reagents. They are controlled based on input detection by sensors based on regenerative surfaces and/or other early detection sensors, and are placed in an active mode only when a potential threat is detected. The network provides the ability to tailor sets of sensors based on an area to be protected in combination with different threat scenarios. In the case of a building or other enclosed structure, both large and small releases, as well as slow and fast releases, of agents may occur either internal or external to the structure. The rate of release is also variable. By correct placement of the sensors, each of these scenarios is quickly detected, and appropriate measures may be taken to minimize damage from the threat. The network may provide input to a heating and ventilation system, or the security management system of the structure in a further embodiment to automate the control response.

In another aspect, the present invention relates to methods of constructing a sensors network. Accordingly, sensors based on a regenerative surface air sampler can be added into a network. The sensors may be of biological particles, or may be of other types such as chemical or radiological sensors.

Figure 9:
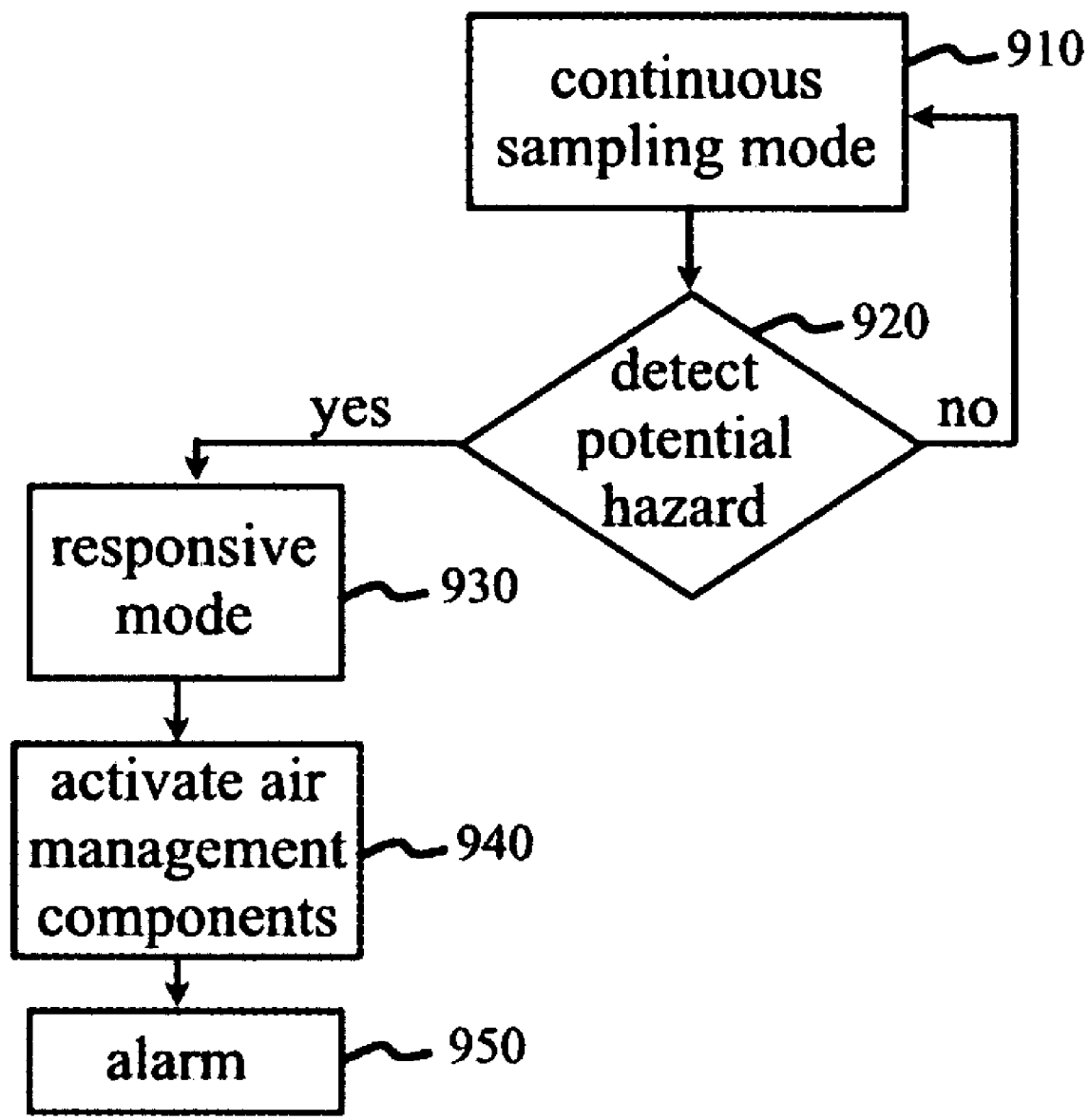
FIG. 9 shows a diagram of a method of controlling ambient air quality.

In yet another aspect the present invention relates to methods of controlling ambient air quality and alerting those potentially affected by airborne hazards (see FIG. 9). According to the invented methods, ambient air is routinely monitored with at least one sensor based on a regenerative surface air sampler in a continuous sampling mode (910). Sampling can take place continuously and automatically for extended periods of time. As long as no potential hazard is detected (920) continuous sampling (910) is performed. If at one time sampling by the sensor indicates a probable threat (920), at least one responsive action is taken performed (930). For example, the responsive step may comprise actuating at least one air management component (940), such as activating at least one specific sensor. A warning signal (950) may also issued immediately upon initial detection of the hazard or after confirmation of the presence of a hazard at a second location. In case an alert signal is issued, it may be transmitted to one or several locations, such as building controller, facility management, and or a fire department or law enforcement agency.

The invention provides several advantages compared to current related technologies, although all advantages are not necessarily present in every embodiment of the invention. Unlike most extractive techniques, the disclosed invention is automatic and requires little or no consumable items. Consequently, it requires human intervention quite rarely, whether for operation, maintenance or service. The technology is thus user friendly, i.e. its use does not require training. In addition, the cost of employing the invented technology is also kept low because consumables are unnecessary.

Unlike in situ detection methods, the invented technology is inexpensive and even allows a more comprehensive analysis of airborne particles. Because aggregates of particles rather than individual particles are subject to characterization, the technology does not require sophisticated equipment like powerful lasers and very sensitive photon counters. Therefore, the invented technology is more affordable. In addition, immobilization of particles makes possible prolonged analysis or multiple analyses of samples. Hence, the invention is compatible with a more thorough sample analysis and consequent increased reliability.

The invented technology allows affordable, automatic, and user friendly monitoring of airborne particles. Consequently, prolonged monitoring of a large number and variety of premises is feasible. Continuous monitoring even of buildings at low risk of biohazard exposure might make a critical difference because noxious biologicals can have devastating effects. Thus, the invention can minimize exposure of persons and expedite protective measures. Moreover, the technology lends itself to integration with other types of monitoring technologies, for example smoke, chemical, and/or radiological alarms, for comprehensive environmental monitoring solutions. In sum, the invented technology permits widespread adoption of airborne biological detectors, resulting in increased security of a large segment of the human population.

The examples presented below are provided as a further guide to a practitioner of ordinary skill in the art, and are not meant to be limiting in any way.

EXAMPLE

Detection of Aerosolized Fluorescent Particles Using a Regenerative Surface

Figure 7:
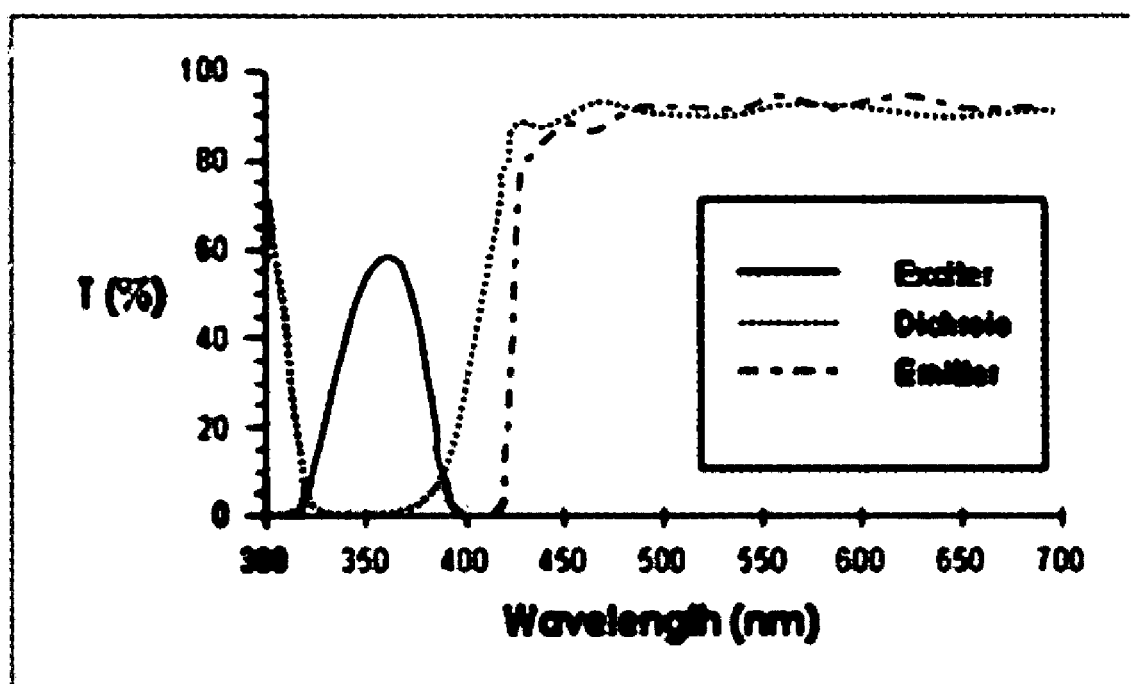
FIG. 7 shows transmission profiles of the dichroic mirror, exciter and emitter filters.

A regenerative surface air sampler based was constructed. The impaction plate was made of aluminum, and was shaped as a lobed cam with three regenerative surfaces. Components of the system included an inertial impactor, a fluorescence detector, and a felt wheel brush surface regenerator. The fluorescence detector was arranged essentially as depicted in FIG. 5, with transmission characteristics of the dichroic mirror, excitation and emission filters as shown in FIG. 7. The UV LED emission was specified to be about 375+/−3 nm.

Biological aerosol was simulated with a fluorescent powder (UVPN UV Powder sold by LDP, LLC (www.maxmax.com)). It was aerosolized by tapping an open envelope of the powder three times, releasing approximately 100 milligrams of the powder into the air several feet away from the air inlet to the sensor.

Figure 8:
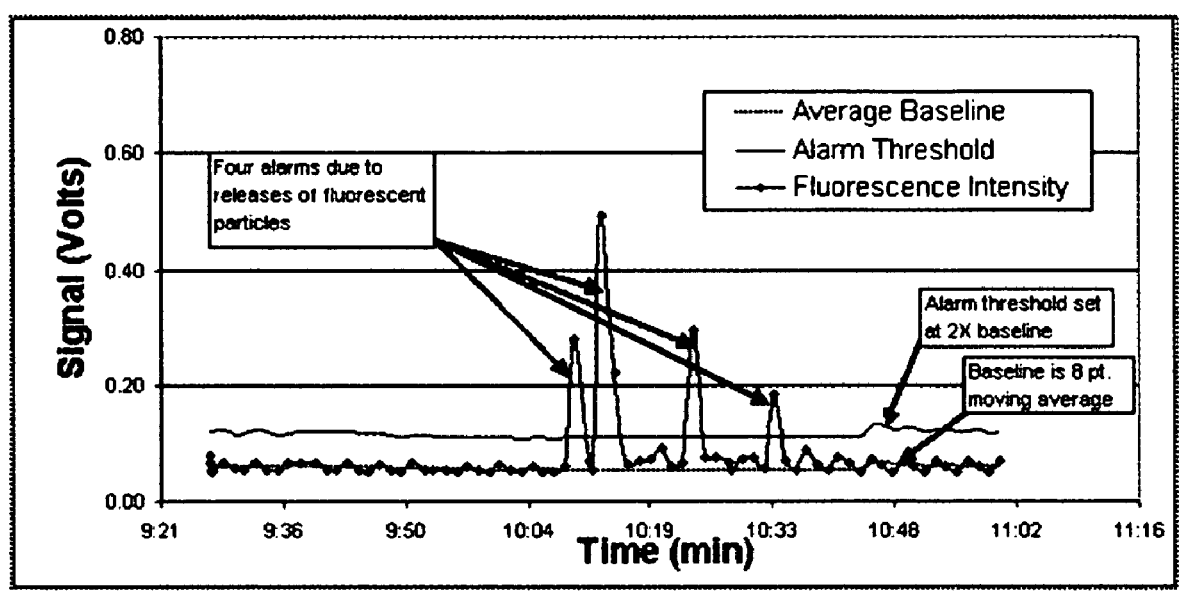
FIG. 8 shows results of testing fluorescent aerosol detection using a regenerative collection surface air sampler.

Results of the test are shown in FIG. 8. As can be seen, the apparatus reliably detected releases of fluorescent particles. It is also noticeable that the baseline value varies slightly for each independent regenerative surface, suggesting that improved accuracy may be achieved using surface specific averages. Note that the algorithm employed for this example holds the baseline at a constant level for the next 10 samples after an alarm.

All cited documents, including patents, patent applications, and other publications are incorporated herein by reference in their entirety.

Foregoing described embodiments of the invention are provided as illustrations and descriptions. They are not intended to limit the invention to the precise form described. Other variations and embodiments are possible in light of above teachings, and it is thus intended that the scope of invention not be limited by this Detailed Description, but rather by the following claims.

What is claimed is:

1. A device comprising:
   a sensor based on a regenerative surface air sampler, the sensor comprising:
      a regenerable collection surface configured to collect particles from the air;
      a surface regenerator configured to remove particles from the regenerable collection surface, such that once regenerated, the regenerable collection surface can collect additional particles from the air, and such that particles collected before regeneration of the regenerable collection surface are substantially no longer present to contaminate particles collected after the regeneration; and
      an analyzer for evaluating the particles collected on the regenerable collection surface; and
   a communication interface coupled to the sensor.

2. The device according to claim 1, wherein the sensor is selected from the group consisting of biological, chemical, and radiological sensors.

3. The device according to claim 1, wherein the communication interface is selected from the group consisting of a transmitter, a transceiver, and an interface that is configured to communicate over an automation system network.

4. The device according to claim 1, wherein the regenerable collection surface is part of an impaction plate.

5. The device according to claim 1, wherein the sensor further comprises a spotting nozzle configured to direct an air stream towards the regenerable collection surface, such that the resulting impact of the air stream with the regenerable collection surface generates a spot of particles on the regenerable collection surface.

6. The device according to claim 1, wherein the surface regenerator comprises at least one element selected from the group consisting essentially of:
   a brush that regenerates the regenerable collection surface by brushing away particles that were collected on the regenerable collection surface;
   a pad that regenerates the regenerable surface by pressing against the regenerable collection surface while there is movement between the pad and the regenerable collection surface relative to each other, so as to remove particles that were collected on the regenerable collection surface; and
   a wheel coupled to a motor that regenerates the regenerable collection surface by pressing against the regenerable collection surface while the motor rotates the wheel, so as to remove particles that were collected on the regenerable collection surface.

7. The device according to claim 1, further comprising a battery backup power supply.

8. The device according to claim 1, further comprising a building, such that the device is incorporated into the building.

9. The device according to claim 1, further comprising an aircraft, such that the device is incorporated into the aircraft.

10. The device according to claim 1, wherein the sensor is capable to output a positive response to the communication interface; and further comprising an air sampler coupled to the communication interface, wherein the air sampler can be activated by the positive response capture at least one sample of airborne particles.

11. The device of claim 1, wherein the surface regenerator comprises at least one element selected from the group consisting essentially of:
   a nozzle configured to direct high velocity air towards the regenerable collection surface to dislodge particles deposited thereon;
   a blade configured to scrape the regenerable collection surface to dislodge particles deposited thereon;
   means for electrostatically charging the collection surface, so that a static charge disperses the particles that were deposited thereon;
   means for directing energy to the particles collected upon the regenerable collection surface to dislodge particles deposited thereon; and
   means for directing energy to the regenerable collection surface to dislodge particles deposited thereon.

12. The device of claim 1, wherein the sensor further comprises at least one element selected from the group consisting of:
   a particle concentrator configured to increase a concentration of airborne particles within a desirable size range in an air stream from which the regenerable collection surface collects particles; and
   a size-selective inlet configured to precondition air from which particles are to be collected by the regenerable collection surface by removing particles from the air that have a size greater than a predefined size.

13. The device of claim 1, wherein the sensor further comprises a mechanically-based homing sensor that positions the regenerable collection surface relative to a selected component, the selected component comprising at least one component selected from the group consisting essentially of:
   a spotting nozzle configured to deposit a spot of particles on the regenerable collection surface;
   the analyzer;
   the surface regenerator; and
   a liquid coating applicator used to apply a liquid to the regenerable collection surface, to moisten the regenerable collection surface prior to collecting the particles, thereby enhancing a collection efficiency of the regenerable collection surface.

14. The device of claim 1, wherein the sensor further comprises
   a processor coupled to the analyzer, the processor being logically configured to determine a concentration of biological particles collected on the regenerable collection surface, and to activate an alarm signal when the processor determines that the concentration of biological particles collected on the regenerable collection surface exceeds a predetermined value.

15. An air monitoring system comprising:
a sensor that includes:
   a regenerable collection surface configured to collect particles from the air, to provide sample particles;
   a surface regenerator configured to remove particles from the collection surface, such that once regenerated, the regenerable collection surface can collect additional particles from the air, particles that were collected before regeneration of the regenerable collection surface being substantially removed by the surface regenerator to avoid contaminating particles collected after the regeneration; and
   an analyzer configured to determine characteristics of the particles collected on the regenerable collection surface;
a communication interface configured to enable the air monitoring system to be coupled to a network; and
a controller coupled to the sensor, the controller being configured to cyclically implement a plurality of functions, including:
   directing airborne particles so that they are deposited on the regenerable collection surface to form a spot;
   analyzing the particles forming the spot;
   transmitting a signal over the communication interface when the analysis indicates the particles represent a potential threat; and
   activating the surface regenerator to regenerate the regenerable collection surface after the particles have been analyzed.

16. An air monitoring system comprising:
a sensor based on a regenerative surface air sampler, the sensor comprising:
   a regenerable collection surface configured to collect particles from the air;
   a surface regenerator configured to remove particles from the regenerable collection surface, such that once regenerated, the regenerable collection surface can collect additional particles from the air, and such that particles collected before regeneration of the regenerable collection surface are substantially no longer present on the regenerable collection surface to contaminate particles collected after the regenerable collection surface is regenerated; and
   an analyzer for evaluating the particles collected on the regenerable collection surface, in order to determine if the collected particles represent a potential threat; and
a controller communicatively coupled to the sensor, the controller being configured to selectively actuate the surface regenerator to regenerate the regenerable collection surface.

17. The system according to claim 16, wherein the sensor is selected from the group consisting of dumb sensors, smart sensors, and intelligent sensors.

18. The system according to claim 16, wherein the controller configured to actuate at least one other component in response to information received from the sensor.

19. The system according to claim 16, wherein the system is associated with air management equipment.

20. A network comprising:
a sensor based on a regenerative surface air sampler, the sensor comprising:
   a regenerable collection surface configured to collect particles from the air;
   a surface regenerator configured to remove particles from the regenerable collection surface, such that once thus regenerated, the regenerable collection surface can collect additional particles from the air, and such that particles collected before regeneration of the regenerable collection surface are substantially no longer present on the regenerable collection surface to contaminate particles collected after the regeneration; and
   means for collecting data corresponding to the particles collected on the regenerable collection surface;
a transceiver for communicating over an automation system network;
at least one actuator;
an air management component coupled to the actuator; and
a controller communicatively coupled to the sensor, the transceiver, and the actuator, the controller being configured to implement a plurality of functions, including:
   analyzing particles collected on the regenerable collection surface using data collected by the sensor;
   transmitting a signal to the automation system network using the transceiver when the analysis indicates the particles represent a potential threat; and
   activating the surface regenerator to regenerate the regenerable collection surface after the particles have been analyzed.

21. The network according to claim 20, wherein the controller actuates the air management component based on information received from the sensor.

22. The network according to claim 20, wherein the surface regenerator comprises at least one element selected from the group consisting essentially of:
   a brush that regenerates the regenerable collection surface by brushing away particles that were collected on the regenerable collection surface;
   a pad that regenerates the regenerable surface by pressing against the regenerable collection surface while there is relative movement between the pad and the regenerable collection surface, so as to remove particles that were collected on the regenerable collection surface; and
   a wheel coupled to a motor that regenerates the regenerable collection surface by pressing against the regenerable collection surface while the motor rotates the wheel, so as to remove particles that were collected on the regenerable collection surface.

23. The network according to claim 20, wherein the air management component is selected from the group consisting of a sample capture device, a sample analysis device, an air duct damper, and a particle counter.

24. A system comprising:
a sensor based on a regenerative surface air sampler, the sensor comprising:
   a regenerable collection surface configured to collect particles from the air;
   a surface regenerator configured to remove particles from the regenerable collection surface, such that once regenerated, the regenerable collection surface can collect additional particles from the air, and such that particles collected before regeneration of the regenerable collection surface are substantially no longer present on the regenerable collection surface to contaminate particles collected after regeneration of the regenerable collection surface; and an analyzer configured to collect data corresponding to the particles collected on the regenerable collection surface;

a transceiver for communicating over an automation system network; and a controller communicatively coupled to the sensor and the transceiver, the controller being configured to implement a plurality of functions, including:

analyzing data collected by the sensor corresponding to the particles collected on the regenerable collection surface to determine if the particles represent a potential threat;

transmitting a signal to the automation system network using the transceiver when the analysis indicates the particles represent a potential threat; and activating the surface regenerator to regenerate the regenerable collection surface after the particles have been analyzed.

25. The system according to claim 24, wherein the controller communicates via at least one technique selected from the group consisting of a BACnet protocol, a wireless communication, an RF link to an RF link network, and a wired link.

26. The system according to claim 24, wherein the surface regenerator comprises at least one element selected from the group consisting essentially of:

a brush that regenerates the regenerable collection surface by brushing away particles that were collected on the regenerable collection surface;

a pad that regenerates the regenerable collection surface by pressing against the regenerable collection surface while the pad and the regenerable collection surface move relative to each other, so as to remove particles that were collected on the regenerable collection surface; and a wheel coupled to a motor for regenerating the regenerable collection surface by pressing against the regenerable collection surface while the motor rotates the wheel, so as to remove particles that were collected on the regenerable collection surface.

27. The system according to claim 24, wherein the sensor further comprises a mechanically-based homing sensor that positions the regenerable collection surface relative to a specific component, the specific component comprising at least one component selected from the group consisting essentially of:

a spotting nozzle configured to deposit a spot of particles on the regenerable collection surface;

the analyzer;

the surface regenerator; and a liquid coating applicator used to apply a liquid to the regenerable collection surface.

28. A method of constructing a network of sensors, the method comprising adding a sensor based on a regenerative surface air sampler to the network, wherein the sensor comprises:

a regenerable collection surface configured to collect particles from the air; and a surface regenerator configured to remove particles from the regenerable collection surface, such that once the regenerable collection surface is regenerated, the regenerable collection surface can collect additional particles from the air, and such that particles collected before regeneration of the regenerable collection surface are substantially no longer present on the regenerable collection surface to contaminate particles collected after the regeneration of the regenerable collection surface.

29. The method according to claim 28, where the network comprises a smoke or fire sensor.

30. A method of controlling ambient air quality, the method comprising:

sampling ambient air with at least one sensor based on a regenerative surface air sampler, the sensor comprising:

a regenerable collection surface configured to collect particles from the air;

a surface regenerator configured to remove particles from the regenerable collection surface, such that once regenerated, the regenerable collection surface can collect additional particles from the air, and such that particles collected before regeneration of the regenerable collection surface are substantially no longer present to contaminate particles collected after the regeneration of the regenerable collection surface; and means for determining if the particles collected on the regenerable collection surface represent a potential threat to air quality; and upon receiving an indication of a probable threat from the sensor, performing a responsive step.

31. The method according to claim 30, wherein the responsive step comprises at least one step selected from the group consisting essentially of actuating an air management component, activating at least one sampler specific sensor, issuing a warning signal, and transmitting an alert signal to facility management.

32. The method according to claim 30, further comprising the step of analyzing particles on the regenerable collection surface to determine whether or not an indication of a probable threat exists.

33. The method according to claim 32, wherein after the step of analyzing the particles, further comprising the step of activating the surface regenerator to remove particles from the regenerable collection surface, such that once regenerated, the regenerable collection surface can collect additional particles from the air, and such that particles collected before regeneration of the regenerable surface are substantially no longer present to contaminate particles collected after the regeneration.

34. The method according to claim 30, wherein the responsive step comprises the step of transmitting an alert signal to a fire department or law enforcement agency.

35. Apparatus configured to collect airborne particles, comprising:

a sensor based on a regenerative surface air sampler, the sensor comprising:

a regenerable collection surface configured to collect particles from the air; and a surface regenerator configured to remove particles from the regenerable collection surface, such that once regenerated, the regenerable collection surface can collect additional particles from the air, and such that particles collected before regeneration of the regenerable collection surface are substantially no longer present to contaminate particles collected after the regeneration; and a communication interface coupled to the sensor.

36. A method for continuously monitoring airborne particles, the method repetitively carrying out a plurality of cycles, each cycle comprising the steps of:

depositing particles that were airborne on a regenerable collection surface;

analyzing the particles that were deposited on the regenerable collection surface;

when analysis indicates that the particles deposited represent a potential threat, transmitting a signal indicative of the potential threat over a network; and regenerating the regenerable collection surface to substantially remove the particles that were deposited thereon during a previous cycle.

37. The method of claim 36, wherein the step of depositing particles on the regenerable collection surface comprises the step of depositing the particles to form a spot.

38. The method of claim 36, wherein the step of regenerating the collection surface comprises at least one step selected from the group of steps consisting essentially of:

brushing the regenerable collection surface, to dislodge the particles deposited on the regenerable collection surface;

pressing a pad against the regenerable collection surface while there is relative motion between the pad and the regenerable collection surface, to remove the particles deposited on the regenerable collection surface;

pressing a wheel against the regenerable collection surface while there is relative motion between the wheel and the regenerable collection surface, to remove the particles deposited on the regenerable collection surface;

directing high velocity air towards the regenerable collection surface to dislodge the particles deposited on the regenerable collection surface;

electrostatically charging the regenerable collection surface to electrostatically disperse the particles deposited on the regenerable collection surface; and directing energy to the particles collected upon the regenerable collection surface to dislodge the particles deposited on the regenerable collection surface.

39. The method of claim 36, further comprising the step of verifying that the step of regenerating the regenerable collection surface has substantially removed the particles that were previously deposited before starting to deposit particles on the regenerable collection surface in a next cycle.

40. The method of claim 39, wherein the step of analyzing the particles that were deposited comprises measuring fluorescence properties of the deposited particles, and the step of verifying that the step of regenerating the regenerable collection surface has substantially removed the particles that were previously deposited comprises the steps of:

determining a background fluorescence level for the regenerated collection surface; and comparing the background fluorescence level with predetermined criteria, such that if the background fluorescence level does not substantially satisfy the predetermined criteria, the step of regenerating is repeated before starting to deposit particles on the regenerable collection surface in a next cycle, until the background fluorescence level substantially satisfies the predetermined criteria.

41. The method of claim 36, wherein the step of analyzing the particles that were deposited comprises at least one step selected from the group consisting of:

pre-treating the particles that were deposited by performing plasma lysing, adding a matrix solution, and measuring a mass spectra of the particles that were deposited and pretreated, using mass spectrometry; and measuring an autofluorescence of any bio-molecules that may be present in the particles that were deposited to obtain a biological signature of the particles, the biological signature being obtained using the steps of:

determining an average value and a standard deviation based on previously obtained estimates of the concentration of biological particles;

comparing the estimated concentration to the average value; and transmitting the signal if the estimated concentration exceeds a sum of the average value and a product of a predetermined factor and the standard deviation.

42. The method of claim 36, wherein the method steps are implemented by a plurality of sensors coupled together to form a network, to enable air monitoring over a wider area than that monitored using a single sensor.

43. The method of claim 36, wherein the step of transmitting the signal indicative of the results over the network comprises at least one step selected from the group of steps consisting essentially of:

activating an alarm signal directed to a designated party;

actuating an air management component;

producing a warning signal;

moving a damper in an air duct;

transmitting an alarm signal to a fire department;

transmitting an alarm signal to a law enforcement agency; and transmitting an alarm signal to a management entity responsible for managing a facility.

* * * * *

UNITED STATES PATENT AND TRADEMARK OFFICE
CERTIFICATE OF CORRECTION

PATENT NO.        : 7,265,669 B2
APPLICATION NO. : 10/791057
DATED               : September 4, 2007
INVENTOR(S)      : Call et al.

It is certified that error appears in the above-identified patent and that said Letters Patent is hereby corrected as shown below:

| | |
|---|---|
| Column 4, line 2 | after "spectrometer" (1st occurrence) insert --or-- |
| Column 5, line 46 | "a" should read --an-- |
| Column 6, line 28 | "preformed" should read --performed-- |
| Column 6, line 34 | delete "calculating" insert therefor --to calculate-- |
| Column 7, line 45 | after "sensor" insert --and-- |
| Column 8, line 12 | after "presence" insert --of-- |
| Column 8, line 58 | "turns" should read --turn-- |
| Column 10, line 10 | "particle" should read --particles-- |
| Column 10, line 15 | after "represent" delete "an" |
| Column 10, line 21 | "mean" should read --meant-- |
| Column 10, line 45 | after "remove" insert --it-- |
| Column 11, line 61 | after "may" insert --be-- |
| Column 12, line 64 | after "oriented" insert --at-- |
| Column 18, line 32 | after "can" insert --be-- |
| Column 19, line 31 | "photo diodes" should read --photo-diodes-- |
| Column 19, line 38 | "becomes" should read --become-- |
| Column 22, line 53 | after "and" delete "by" |

UNITED STATES PATENT AND TRADEMARK OFFICE
CERTIFICATE OF CORRECTION

PATENT NO. : 7,265,669 B2  
APPLICATION NO. : 10/791057  
DATED : September 4, 2007  
INVENTOR(S) : Call et al.

Page 2 of 2

It is certified that error appears in the above-identified patent and that said Letters Patent is hereby corrected as shown below:

| | |
|---|---|
| Column 25, line 10 | after "components" insert --of-- |
| Column 26, line 3 | after "is" delete "taken" |
| Column 26, line 7 | "issued" should read --issue-- |
| Column 26, line 58 | "based" should appear after "surface" instead of after "sampler" |
| Column 29, line 60 (Claim 18, line 2) | after "controller" insert --is-- |

Signed and Sealed this

Eighth Day of July, 2008

JON W. DUDAS  
*Director of the United States Patent and Trademark Office*